(12) United States Patent
Thullier et al.

(10) Patent No.: US 9,012,608 B2
(45) Date of Patent: Apr. 21, 2015

(54) G IMMUNOGLOBULIN USED AGAINST ANTHRAX TOXINS

(75) Inventors: Philippe Thullier, Bernin (FR); Christian Behrens, Palaiseau (FR)

(73) Assignees: Laboratoire Francais du Fractionnement et des Biotechnologies, Les Ulis (FR); Etat Francais Represente Par le Delegue General de l'Armement, Armees (FR)

( * ) Notice: Subject to any disclaimer, the term of this patent is extended or adjusted under 35 U.S.C. 154(b) by 477 days.

(21) Appl. No.: 12/744,756

(22) PCT Filed: Nov. 28, 2008

(86) PCT No.: PCT/FR2008/052160
§ 371 (c)(1),
(2), (4) Date: May 26, 2010

(87) PCT Pub. No.: WO2009/071860
PCT Pub. Date: Jun. 11, 2009

(65) Prior Publication Data
US 2011/0201033 A1 Aug. 18, 2011

(30) Foreign Application Priority Data
Nov. 29, 2007 (FR) ...................................... 07 59419

(51) Int. Cl.
*C12P 21/08* (2006.01)
*C07K 16/12* (2006.01)
*A61K 39/00* (2006.01)

(52) U.S. Cl.
CPC ....... *C07K 16/1278* (2013.01); *A61K 2039/505* (2013.01); *A61K 2039/545* (2013.01); *C07K 2316/96* (2013.01); *C07K 2317/21* (2013.01); *C07K 2317/24* (2013.01); *C07K 2317/55* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| 2006/0121045 | A1  |      6/2006 | Iverson et al.              |
|--------------|-----|-------------|-----------------------------|
| 2007/0269369 | A1* |     11/2007 | Gegg et al. .......... 424/1.41 |
| 2011/0033450 | A1* |      2/2011 | Thullier .............. 424/133.1 |

FOREIGN PATENT DOCUMENTS

| WO | 2007/084107 A2 | 7/2007 |
| WO | 2009/050388 A1 | 4/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
International Search Report, dated Jul. 15, 2009, from corresponding PCT application.
Emmanuelle Laffly et al., "Selection of a Macaque Fab with Framework Regions Like Those in Humans, High Affinity, and Ability to Neutralize the Protective Antigen (PA) of *Bacillus anthracis* by Binding to the Segment of PA between Residues 686 and 694", Antimicrobial Agents and Chemotherapy, Aug. 2005, pp. 3414-3420, vol. 49, No. 8, XP-002444247; Cited in International Search Report.
Kim L. Wark et al., "Latest technologies for the enhancement of antibody affinity", Advanced Drug Delivery Reviews, Aug. 7, 2006, pp. 657-670, vol. 58, No. 5-6; Cited in International Search Report.
Leonard G. Presta et al, Abstract of "Engineering of therapeutic antibodies to minimize immunogenicity and optimize function", Advanced Drug Delivery Reviews, Aug. 7, 2006, pp. 640-656, vol. 58, No. 5-6; Cited in International Search Report.
Emmanuelle Laffly et al., "Improvement of an Antibody Neutralizing the Anthrax Toxin by Simultaneous Mutagenesis of Its Six Hypervariable Loops", Journal of Molecular Biology, 2008, pp. 1094-1103, vol. 378, No. 5; Cited in International Search Report.
Barbas III et al., "In vitro evolution of a neutralizing human antibody to human immunodeficiency virus type 1 to enhance affinity and broaden strain cross-reactivity", Proc. Natl. Acad. Sci. USA, Medical Sciences, 1994, vol. 91, pp. 3809-3813.
Hamilton, Robert G., "Molecular Engineering: Applications to the Clinical Laboratory", Clinical Chemistry, 1993, vol. 39, No. 9, pp. 1988-1997.
Hawkins et al., "Selection of Phage Antibodies by Binding Affinity—Mimicking Affinity Maturation", J. Mol. Biol., 1992, vol. 226, pp. 889-896.
Jackson et al., "In Vitro Antibody Maturation—Improvement of a High Affinity, Neutralizing Antibody Against IL-1β", The Journal of Immunology, 1995, vol. 154, pp. 3310-3319.
Marks et al., "By-Passing Immunization: Building High Affinity Human Antibodies by Chain Shuffling", Biotechnology, 1992, vol. 10, pp. 779-783.
Schier et al., "Identification of functional and structural amino-acid residues by parsimonious mutagenesis", Gene, 1996, vol. 169, pp. 147-155.
Yelton et al., "Affinity Maturation of the BR96 Anti-Carcinoma Antibody by Codon-Based Mutagenesis", The Journal of Immunology, 1995, vol. 155, pp. 1994-2004.

* cited by examiner

*Primary Examiner* — Brad Duffy
(74) *Attorney, Agent, or Firm* — Young & Thompson

(57) ABSTRACT

An immunoglobulin of the G class (IgG) directed against the protective antigen (PA) of the anthrax toxin, includes:
- a light-chain variable region including an amino-acid sequence having at least 90% amino-acid identity with the sequence SEQ ID No1 such as defined in the description, and
- a heavy-chain variable region including an amino-acid sequence having at least 90% amino-acid identity with the sequence SEQ ID No2 such as defined in the description, characterized in that it consists of an IgG1 or an IgG2.

15 Claims, 16 Drawing Sheets of the prior application FR 07 06744

35H

Figure 1
of the prior application FR 07 06744 (cont'd)

—NdeI—

—V6 da V2ctggatatcaaacgaactgtgctgaccaaatgtcttcatc
agcaggacagacgtatacaccctc————gacctatagttgcttgacaccgaacgtggttcacagaagtag ←——————————Amplicon 4 327 bases——————————→

Figure 1 (cont'd)

Challenge

Doxycycline discontinuation in the presence or absence of IgG 35PA83 injection

[Survival curve showing Percent survival vs Time (hours) after treatment, 0-600 hours]

—○— Control

—◇— Doxycycline (5 mg/kg/day)

—◆— Doxycycline (5mg/kg/day) + IgG 35PA83 (1 mg/kg)
(***: significant effect vs doxycycline, p<0.0001)

—▽— Doxycycline (5mg/kg/day) + IgG 35PA83 (2mg/kg)
(***: significant effect vs doxycycline, p<0.0001)

Figure 7

```
                        SEQUENCE LISTING

<160> NUMBER OF SEQ ID NOS: 37

<210> SEQ ID NO 1
<211> LENGTH: 103
<212> TYPE: PRT
<213> ORGANISM: Macaca fascicularis

<400> SEQUENCE: 1
```

Thr Gln Ser Pro Ser Ser Leu Ser Ala Tyr Val Gly Asp Lys Val Thr
1               5                   10                  15

Ile Thr Cys His Ala Ser Gln Gly Ile Asn Ser Trp Leu Ala Trp Tyr
            20                  25                  30

Gln Gln Lys Pro Gly Lys Ala Pro Lys Leu Leu Ile Tyr Lys Ala Ser
        35                  40                  45

Ser Leu Gln Ser Gly Val Pro Ser Arg Phe Ser Gly Ser Gly Ser Gly
    50                  55                  60

Thr Asp Tyr Thr Leu Thr Ile Ser Ser Leu Gln Ser Glu Asp Phe Ala
65                  70                  75                  80

Ser Tyr Tyr Cys Leu Gln Tyr Asp Ser Ala Pro Leu Ala Phe Gly Pro
                85                  90                  95

Gly Thr Lys Leu Asp Ile Lys
            100

<210> SEQ ID NO 2
<211> LENGTH: 119
<212> TYPE: PRT
<213> ORGANISM: Macaca fascicularis

<400> SEQUENCE: 2

Ser Gly Pro Gly Leu Leu Lys Pro Ser Glu Thr Leu Ser Leu Thr Cys
1               5                   10                  15

Ala Val Ser Gly Asp Ser Ile Ser Ser Gly Tyr Tyr Trp Ser Trp Ile
            20                  25                  30

Arg Gln Ser Pro Gly Lys Gly Leu Glu Trp Ile Gly His Ile Tyr Gly
        35                  40                  45

Ser Thr Ala Asp Thr Lys Tyr Asn Pro Ser Leu Arg Ser Arg Val Thr
    50                  55                  60

Ile Ser Lys Asp Thr Ser Lys Asn Gln Leu Ser Leu Gln Leu Arg Ser
65                  70                  75                  80

Val Thr Ala Ala Asp Thr Ala Val Tyr Tyr Cys Ala Arg Ser Gly Tyr
                85                  90                  95

Asn Phe Trp Ser Gly Glu Tyr Tyr Gly Leu Asp Ser Trp Gly Gln Gly
            100                 105                 110

Ala Val Val Thr Val Ser Ser
        115

<210> SEQ ID NO 3
<211> LENGTH: 107
<212> TYPE: PRT
<213> ORGANISM: Homo sapiens

<400> SEQUENCE: 3

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 210
<212> TYPE: PRT
<213> ORGANISM: Artificial Sequence
<220> FEATURE:
<223> OTHER INFORMATION: Synthetic Peptide

<400> SEQUENCE: 5

```
Thr Gln Ser Pro Ser Ser Leu Ser Ala Tyr Val Gly Asp Lys Val Thr
1               5                   10                  15

Ile Thr Cys His Ala Ser Gln Gly Ile Asn Ser Trp Leu Ala Trp Tyr
            20                  25                  30

Gln Gln Lys Pro Gly Lys Ala Pro Lys Leu Leu Ile Tyr Lys Ala Ser
        35                  40                  45

Ser Leu Gln Ser Gly Val Pro Ser Arg Phe Ser Gly Ser Gly Ser Gly
    50                  55                  60

Thr Asp Tyr Thr Leu Thr Ile Ser Ser Leu Gln Ser Glu Asp Phe Ala
65                  70                  75                  80

Ser Tyr Tyr Cys Leu Gln Tyr Asp Ser Ala Pro Leu Ala Phe Gly Pro
                85                  90                  95

Gly Thr Lys Leu Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210
```

<210> SEQ ID NO 6
<211> LENGTH: 449
<212> TYPE: PRT
<213> ORGANISM: Artificial Sequence
<220> FEATURE:
<223> OTHER INFORMATION: Synthetic Peptide

<400> SEQUENCE: 6

```
Ser Gly Pro Gly Leu Leu Lys Pro Ser Glu Thr Leu Ser Leu Thr Cys
1               5                   10                  15

Ala Val Ser Gly Asp Ser Ile Ser Ser Gly Tyr Tyr Trp Ser Trp Ile
            20                  25                  30

Arg Gln Ser Pro Gly Lys Gly Leu Glu Trp Ile Gly His Ile Tyr Gly
        35                  40                  45

Ser Thr Ala Asp Thr Lys Tyr Asn Pro Ser Leu Arg Ser Arg Val Thr
    50                  55                  60

Ile Ser Lys Asp Thr Ser Lys Asn Gln Leu Ser Leu Gln Leu Arg Ser
65                  70                  75                  80

Val Thr Ala Ala Asp Thr Ala Val Tyr Tyr Cys Ala Arg Ser Gly Tyr
                85                  90                  95

Asn Phe Trp Ser Gly Glu Tyr Tyr Gly Leu Asp Ser Trp Gly Gln Gly
            100                 105                 110

Ala Val Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 7
<211> LENGTH: 309
<212> TYPE: DNA
<213> ORGANISM: Macaca fascicularis

<400> SEQUENCE: 7
acccagtctc catcgtccct gtctgcatat gtgggagaca agtcaccat cacttgccat      60 gccagtcagg gtattaacag ttggttagcc tggtatcagc agaaaccagg gaaagcccct    120
aaacttctga tctataaggc gtccagtttg caaagtgggg tcccatcaag gttcagcggc    180
agtggatctg ggacagatta tactctcacc atcagcagct tgcagtctga agactttgct    240
```

```
tcttattact gtctacaata tgacagtgcc ccattggctt tcggcccegg gaccaagctg    300 gatatcaaa                                                            309

<210> SEQ ID NO 8
<211> LENGTH: 363
<212> TYPE: DNA
<213> ORGANISM: Macaca fascicularis

<400> SEQUENCE: 8
caggagtcgg gaccaggact gctgaagcct tcggaaaccc tgtccctcac ctgcgctgtc     60
tctggtgact ccatcagcag cggttactac tggagctgga tccgccagtc cccagggaag    120
gggctggagt ggattgggca tatctatggt agtactgcgg acaccaagta caacccctcc    180
ctcaggagtc gagtcaccat ttcaaaagac acgtccaaga accagctctc cctgcaactg    240
aggtctgtga ccgccgcgga cacggccgtg tattattgtg cgagatcggg ttacaatttt    300
tggagtggtg aatattacgg tttggattcc tggggccaag gggccgtcgt caccgtctcc    360
tca                                                                  363

<210> SEQ ID NO 9
<211> LENGTH: 990
<212> TYPE: DNA
<213> ORGANISM: Homo sapiens

<400> SEQUENCE: 9
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggggga    360 ccgtcagtct tcctcttccc cccaaaaccc aaggacaccc tcatgatctc ccggaccect    420 gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990

<210> SEQ ID NO 10
<211> LENGTH: 321
<212> TYPE: DNA
<213> ORGANISM: Homo sapiens

<400> SEQUENCE: 10
cgaactgtgg ctgcaccaag tgtcttcatc ttcccgccat ctgatgagca gttgaaatct     60
```

| | |
|---|---:|
| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg t | 321 |

<210> SEQ ID NO 11
<211> LENGTH: 630
<212> TYPE: DNA
<213> ORGANISM: Artificial Sequence
<220> FEATURE:
<223> OTHER INFORMATION: Synthetic Nucleotide

<400> SEQUENCE: 11

| | |
|---|---:|
| acccagtctc catcgtccct gtctgcatat gtgggagaca aagtcaccat cacttgccat | 60 |
| gccagtcagg gtattaacag ttggttagcc tggtatcagc agaaaccagg gaaagcccct | 120 |
| aaacttctga tctataaggc gtccagtttg caaagtgggg tcccatcaag gttcagcggc | 180 |
| agtggatctg ggacagatta tactctcacc atcagcagct gcagtctga agactttgct | 240 |
| tcttattact gtctacaata tgacagtgcc ccattggctt tcggcccgg gaccaagctg | 300 |
| gatatcaaac gaactgtggc tgcaccaagt gtcttcatct tcccgccatc tgatgagcag | 360 |
| ttgaaatctg gaactgcctc tgttgtgtgc ctgctgaata acttctatcc cagagaggcc | 420 |
| aaagtacagt ggaaggtgga taacgccctc caatcgggta actcccagga gagtgtcaca | 480 |
| gagcaggaca gcaaggacag cacctacagc ctcagcagca ccctgacgct gagcaaagca | 540 |
| gactacgaga acacaaagt ctacgcctgc gaagtcaccc atcagggcct gagctcgccc | 600 |
| gtcacaaaga gcttcaacag gggagagtgt | 630 |

<210> SEQ ID NO 12
<211> LENGTH: 1353
<212> TYPE: DNA
<213> ORGANISM: Artificial Sequence
<220> FEATURE:
<223> OTHER INFORMATION: Synthetic Nucleotide

<400> SEQUENCE: 12

| | |
|---|---:|
| caggagtcgg gaccaggact gctgaagcct tcggaaaccc tgtccctcac ctgcgctgtc | 60 |
| tctggtgact ccatcagcag cggttactac tggagctgga tccgccagtc cccagggaag | 120 |
| gggctggagt ggattgggca tatctatggt agtactgcgg acaccaagta caaccctcc | 180 |
| ctcaggagtc gagtcaccat ttcaaaagac acgtccaaga accagctctc cctgcaactg | 240 |
| aggtctgtga ccgccgcgga cacggccgtg tattattgtg cgagatcggg ttacaatttt | 300 |
| tggagtggtg aatattacgg tttggattcc tggggccaag gggccgtcgt caccgtctcc | 360 |
| tcagcctcca caagggccc atcggtcttc ccctggcac ctcctccaa gagcacctct | 420 |
| gggggcacag cggccctggg ctgcctggtc aaggactact cccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |

```
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag ccccatcga gaaaaccatc    1020 tccaaagcca aagggcagcc ccgagaacca caggtgtaca ccctgccccc atcccgggat    1080
gagctgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353
```

<210> SEQ ID NO 13
<211> LENGTH: 78
<212> TYPE: DNA
<213> ORGANISM: Artificial Sequence
<220> FEATURE:
<223> OTHER INFORMATION: Synthetic Primer

<400> SEQUENCE: 13

```
atggacatga gggtccccgc tcagctcctg gggcttctgc tgctctggct cccaggtgcc    60
agatgtgcca tccagttg                                                   78
```

<210> SEQ ID NO 14
<211> LENGTH: 47
<212> TYPE: DNA
<213> ORGANISM: Artificial Sequence
<220> FEATURE:
<223> OTHER INFORMATION: Synthetic Primer

<400> SEQUENCE: 14

```
ctcagtacta gtgccgccac catggacatg agggtccccg ctcagct                   47
```

<210> SEQ ID NO 15
<211> LENGTH: 44
<212> TYPE: DNA
<213> ORGANISM: Artificial Sequence
<220> FEATURE:
<223> OTHER INFORMATION: Synthetic Primer

<400> SEQUENCE: 15

```
acctgggagc cagagcagca gaagccccag gagctgagcg ggga                      44
```

<210> SEQ ID NO 16
<211> LENGTH: 43
<212> TYPE: DNA
<213> ORGANISM: Artificial Sequence
<220> FEATURE:
<223> OTHER INFORMATION: Synthetic Primer

<400> SEQUENCE: 16

```
tgctctggct cccaggtgcc agatgtgcca tccagttgac cca                       43
```

<210> SEQ ID NO 17
<211> LENGTH: 45
<212> TYPE: DNA
<213> ORGANISM: Artificial Sequence
<220> FEATURE:
<223> OTHER INFORMATION: Synthetic Primer

<400> SEQUENCE: 17

```
ctcccacata tgcagacagg gacgatggag actgggtcaa ctgga         45
```

<210> SEQ ID NO 18
<211> LENGTH: 47
<212> TYPE: DNA
<213> ORGANISM: Artificial Sequence
<220> FEATURE:
<223> OTHER INFORMATION: Synthetic Primer

<400> SEQUENCE: 18

```
ctcagtacta gtgccgccac catggacatg agggtccccg ctcagct       47
```

<210> SEQ ID NO 19
<211> LENGTH: 45
<212> TYPE: DNA
<213> ORGANISM: Artificial Sequence
<220> FEATURE:
<223> OTHER INFORMATION: Synthetic Primer

<400> SEQUENCE: 19

```
ctcccacata tgcagacagg gacgatggag actgggtcaa ctgga         45
```

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20

```
tcgtccctgt ctgcatatgt gggag                               25
```

<210> SEQ ID NO 21
<211> LENGTH: 42
<212> TYPE: DNA
<213> ORGANISM: Artificial Sequence
<220> FEATURE:
<223> OTHER INFORMATION: Synthetic Primer

<400> SEQUENCE: 21

```
gatgaagaca cttggtgcag ccacagttcg tttgatatcc ag            42
```

<210> SEQ ID NO 22
<211> LENGTH: 47
<212> TYPE: DNA
<213> ORGANISM: Artificial Sequence
<220> FEATURE:
<223> OTHER INFORMATION: Synthetic Primer

<400> SEQUENCE: 22

```
ctcagtacta gtgccgccac catggacatg agggtccccg ctcagct       47
```

<210> SEQ ID NO 23
<211> LENGTH: 42
<212> TYPE: DNA
<213> ORGANISM: Artificial Sequence
<220> FEATURE:
<223> OTHER INFORMATION: Synthetic Primer

<400> SEQUENCE: 23

```
gatgaagaca cttggtgcag ccacagttcg tttgatatcc ag            42
```

<210> SEQ ID NO 24
<211> LENGTH: 76
<212> TYPE: DNA
<213> ORGANISM: Artificial Sequence

```
<220> FEATURE:
<223> OTHER INFORMATION: Synthetic Primer

<400> SEQUENCE: 24
atgaaacatc tgtggttctt ccttctcctg gtggcagctc ccagatgggt cctgtcccag       60
gtgcagctgc aggagt                                                      76

<210> SEQ ID NO 25
<211> LENGTH: 47
<212> TYPE: DNA
<213> ORGANISM: Artificial Sequence
<220> FEATURE:
<223> OTHER INFORMATION: Synthetic Primer

<400> SEQUENCE: 25
ctcagtgcta gcgccgccac catgaaacat ctgtggttct tccttct                    47

<210> SEQ ID NO 26
<211> LENGTH: 39
<212> TYPE: DNA
<213> ORGANISM: Artificial Sequence
<220> FEATURE:
<223> OTHER INFORMATION: Synthetic Primer

<400> SEQUENCE: 26
cccatctggg agctgccacc aggagaagga agaaccaca                             39

<210> SEQ ID NO 27
<211> LENGTH: 42
<212> TYPE: DNA
<213> ORGANISM: Artificial Sequence
<220> FEATURE:
<223> OTHER INFORMATION: Synthetic Primer

<400> SEQUENCE: 27
tggcagctcc cagatgggtc ctgtcccagg tgcagctgca gg                         42

<210> SEQ ID NO 28
<211> LENGTH: 35
<212> TYPE: DNA
<213> ORGANISM: Artificial Sequence
<220> FEATURE:
<223> OTHER INFORMATION: Synthetic Primer

<400> SEQUENCE: 28
cagtcctggt cccgactcct gcagctgcac ctggg                                 35

<210> SEQ ID NO 29
<211> LENGTH: 47
<212> TYPE: DNA
<213> ORGANISM: Artificial Sequence
<220> FEATURE:
<223> OTHER INFORMATION: Synthetic Primer

<400> SEQUENCE: 29
ctcagtgcta gcgccgccac catgaaacat ctgtggttct tccttct                    47

<210> SEQ ID NO 30
<211> LENGTH: 35
<212> TYPE: DNA
<213> ORGANISM: Artificial Sequence
<220> FEATURE:
<223> OTHER INFORMATION: Synthetic Primer

<400> SEQUENCE: 30
```

```
cagtcctggt cccgactcct gcagctgcac ctggg                              35

<210> SEQ ID NO 31
<211> LENGTH: 27
<212> TYPE: DNA
<213> ORGANISM: Artificial Sequence
<220> FEATURE:
<223> OTHER INFORMATION: Synthetic Primer

<400> SEQUENCE: 31
cagctgcagg agtcgggacc aggactg                                       27

<210> SEQ ID NO 32
<211> LENGTH: 38
<212> TYPE: DNA
<213> ORGANISM: Artificial Sequence
<220> FEATURE:
<223> OTHER INFORMATION: Synthetic Primer

<400> SEQUENCE: 32
accgatgggc ccttggtgga ggctgaggag acggtgac                           38

<210> SEQ ID NO 33
<211> LENGTH: 47
<212> TYPE: DNA
<213> ORGANISM: Artificial Sequence
<220> FEATURE:
<223> OTHER INFORMATION: Synthetic Primer

<400> SEQUENCE: 33
ctcagtgcta gcgccgccac catgaaacat ctgtggttct tccttct                 47

<210> SEQ ID NO 34
<211> LENGTH: 38
<212> TYPE: DNA
<213> ORGANISM: Artificial Sequence
<220> FEATURE:
<223> OTHER INFORMATION: Synthetic Primer

<400> SEQUENCE: 34
accgatgggc ccttggtgga ggctgaggag acggtgac                           38

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
gctcgataca ataaacgcca                                               20

<210> SEQ ID NO 36
<211> LENGTH: 21
<212> TYPE: DNA
<213> ORGANISM: Artificial Sequence
<220> FEATURE:
<223> OTHER INFORMATION: Synthetic Primer

<400> SEQUENCE: 36
tctgggatag aagttattca g                                             21

<210> SEQ ID NO 37
<211> LENGTH: 23
<212> TYPE: DNA
<213> ORGANISM: Artificial Sequence
```

```
<220> FEATURE:
<223> OTHER INFORMATION: Synthetic Nucleotide

<400> SEQUENCE: 37
ggaagtagtc cttgaccagg cag                                      23
```

G IMMUNOGLOBULIN USED AGAINST ANTHRAX TOXINS

FIELD OF THE INVENTION

The present invention relates to a primatized G immunoglobulin directed against PA sub-unit (protective antigen) of bacterium *Bacillus anthracis*.

PRIOR ART

Anthrax is an infectious disease caused by a Gram positive bacterium, *Bacillus anthracis*. This bacterium is non mobile, and forms highly resistant spores, germinating to a vegetative form when present in environments such as human or animal blood or tissues. Although being very resistant, the spores do not duplicate, but they may on the other hand survive for decades in soil.

Anthrax toxin-mediated infections can occur in the three following forms: cutaneous, pulmonary or digestive. The lung infection is the most frequently mortal. Upon inhalation, *B. anthracis* spores come through the alveoli where they are phagocyted by macrophages and dendritic cells, in particular. The spores germinate in these cells and the vegetative forms do multiply within lymph nodes. Bacteria then pass into the blood circulation, do continuously duplicate and produce toxins, partly responsible for the lethal character of the disease. Anthrax toxins are composed of three distinct proteins: the protective antigen (PA, 83 kDa before intracellular enzymatic cleavage and 63 kDa after cleavage), the lethal factor (LF, 90 kDa) and the edema factor (EF, 89 kDa). The lethal toxin is formed of PA and LF; and the edema toxin, which role is less pronounced in the disease physiology, of PA and EF.

These proteins are secreted through the bacterium as non toxic monomers, and gather together on the surface of target cells to form toxic complexes.

Until now, a plurality of antibiotics, such as penicillin, doxycycline and fluoroquinones (for example ciprofloxacin), have been used for treating anthrax infections.

However, some of these antibiotics may have no effect on some strains, which are resistant to antibiotics. Particularly, some of these treatments could be unusable against terrorism or in a bacteriological war context, where antibiotic-resistant strains could be voluntarily disseminated.

In addition, as antibiotics cannot inhibit the anthrax toxin action, it is necessary for these antibiotics to be administered in the early stages of the infection, but early diagnoses are difficult to establish because the initial symptoms are non specific.

Vaccines, which major component is the protective antigen PA, have been developed but are only used for persons which are strongly suspected to have been in contact with *B. anthracis*. In addition, due to the period of several months required for acquiring a sufficient immunity, these vaccines cannot be used in emergency situations. Today in France, none of these vaccines are approved for human use. It is therefore necessary to develop new therapeutic and prophylactic approaches, different from antibiotics.

Passive immunization through antibodies is an efficient strategy for neutralizing the toxin. Several attempts have been made to neutralize the anthrax lethal toxin using monoclonal antibodies directed against the protective antigen (PA) and the lethal factor (LF). Neutralizing the anthrax lethal toxin through the use of an antibody may be effected by inhibiting the binding of PA and its cell receptor, by inhibiting the PA cleavage, by inhibiting the binding of PA to LF or by inhibiting the LF action for example.

The development of novel antibodies that would be able to neutralize the anthrax toxin is therefore of general interest for preventing and efficiently treating anthrax.

In a recent work, a macaque has been immunized with the protective antigen PA83 to obtain antibodies intended to treat the anthrax toxin-mediated human infection. From bone marrow, the inventors have amplified genes encoding PA83-specific antibody fragments and have cloned the same in order to build a library.

A high affinity (Kd=3.4 nM) and strongly neutralizing fragment (50% inhibition concentration=5.6+/−0.13 nM), referred to as 35PA83, has been then isolated (Laffly and al., antimicrobial agents and chemotherapy, 2005, 49(8): 3414-3420).

The immunoglobulin fragment 35PA83 neutralizes the anthrax toxin by preventing any interaction of PA with its cell receptor.

However, in preparation for applying this immunoglobulin fragment to a medical (either prophylactic or therapeutic) use, the improvement of its affinity could advantageously reduce the amount to be administered to the patient as well as the treatment costs. On the other hand, because of the simian origin of this immunoglobulin fragment, it could present a risk of immunogenicity and an alteration of its human bioavailability.

SUMMARY OF THE INVENTION

It is therefore an object of the present invention to provide an entire immunoglobulin, of the IgG1 or IgG2 isotype, directed against antigen PA, obtained from the immunoglobulin fragment 35PA83, that would have been beforehand modified so as to improve its affinity for the antigen and to have a greater similarity with human antibodies.

It is thus an object of the present invention to provide an immunoglobulin of the G class (IgG) directed against the protective antigen (PA) of the anthrax toxin, comprising the variable regions of antibody 35PA83, a few residues of which would have been mutated, and some constant regions of human origin.

It is a further object of the present invention to provide a nucleic acid encoding the IgG of the invention, as well as a vector comprising such nucleic acid, and a host cell containing this vector.

It is also an object of the present invention to provide a composition comprising the IgG of the invention as well as a pharmaceutical composition comprising the IgG.

It is a further object of the present invention to provide the use of the IgG of the invention for preparing a medication for treating or preventing an infection with *Bacillus anthracis*.

The present invention also relates to an anthrax toxin detection kit, a method for detecting in vitro anthrax toxin, as well as an immunoconjugate containing the IgG of the invention.

DESCRIPTION OF THE INVENTION

It is thus an object of the present invention to provide an immunoglobulin of the G class (IgG) directed against the protective antigen (PA) of the anthrax toxin, that comprises:
  a light-chain variable region comprising an amino-acid sequence having at least 90% amino-acid identity with the sequence SEQ ID No1, and
  a heavy-chain variable region comprising an amino-acid sequence having at least 90% amino-acid identity with the sequence SEQ ID No2, and comprising the amino-acid residues corresponding respectively to the serine residue at position 25, the lysine residue at position 54 and the arginine residue at position 60, characterized in that it consists of an IgG1 or an IgG2.

According to the invention, a first nucleic acid having at least 90% identity with a second nucleic acid of reference, will have at least 90%, preferably at least 91%, 92%, 93%, 94%, 95%, 96%, 97%, 97.5%, 98%, 98.3% 98.6%, 99%, 99.6% nucleotide identity with the said second nucleic acid of reference.

According to the invention, a first polypeptide that has at least 90% identity with a second polypeptide of reference, will have at least 90%, preferably at least 91%, 92%, 93%, 94%, 95%, 96%, 97%, 97.5%, 98%, 98.3% 98.6%, 99%, 99.6% amino-acid identity with the said second polypeptide of reference.

As used herein, the "percentage of identity" between two nucleic acid sequences or between two polypeptide sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be effected by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

As regards the annotation of mutations on the light-chain variable region and on the heavy-chain variable region of an antibody of the invention, and more generally any complement to the description of some embodiments of the antibody of the invention, the person skilled in the art may refer to the specification of the French patent application No FR 07/06744 filed on 26 Sep. 2007 for an "antibody used against anthrax toxins", which content is appended thereto at the end of the present specification, from page 48 to page 75.

The presence of a serine residue at position 25 of the sequence SEQ ID No 2 corresponds to the mutation noted "31A" on portion "35H" on FIG. 11, where such mutation may also be referred to as "G/S (31A)".

The presence of a lysine residue at position 54 of the sequence SEQ ID No 2 corresponds to mutation "66" on portion "35H" on FIG. 11, where such mutation may also be referred to as "R/K (66)".

The presence of an arginine residue at position 60 of the sequence SEQ ID No 2 corresponds to a mutation that can be referred to as "K/R (73)" and corresponds to the arginine residue at position 73 on portion "35H" on FIG. 11.

According to the invention, the residues "corresponding" to a serine residue at position 25, a lysine residue at position 54 and an arginine residue at position 60 consist of the hereabove mentioned residues, and:
  (i) which are located at the same position in the sequence that is at least 90% identical with the sequence SEQ ID No2, or
  (ii) which are located at a distinct position, for example due to the fact that the sequence that is 90% identical with the sequence SEQ ID No2 includes one or more deletion(s) or addition(s) of amino-acid(s), as compared to the sequence SEQ ID No 2 acting as a reference.

It is another object of the invention to provide an immunoglobulin of the G class (IgG) such as defined hereabove, characterized in that it contains:
  a light-chain variable region having an amino-acid sequence illustrated by the sequence SEQ ID No 1, and
  a heavy-chain variable region having an amino-acid sequence illustrated by the sequence SEQ ID No 2.

The immunoglobulin fragment 35PA83, composed of a light chain and of a Fd fragment, has been obtained by immunizing a macaque with the protective antigen PA83 of anthrax, as described in Laffly et al. (2005).

The affinity "$K_D$" of an antibody may be measured through the conventional methods known from the person skilled in the art.

The parental, unmodified antibody (i.e. non mutated) 35PA83 has an affinity $K_D$ of $3.4 \ 10^{-9}$ M. This affinity constant has been calculated from the association and dissociation constants measured in real time through surface plasmon resonance, as explained in the examples.

The light-chain variable region of the IgG of the invention (SEQ ID No1) is derived from the light-chain variable region of the immunoglobulin fragment 35PA83, which sequence can be obtained from computerized data banks, like Genbank, under the accession numbers CAH17921 and AJ810487.

Advantageously, the light-chain variable region of the IgG of the invention, having an amino-acid sequence illustrated by the sequence SEQ ID No1, additionally comprises at least one mutation selected from:
  none/A (1)
  none/I (2)
  none/Q (3)
  none/L (4)
  Y/S (14)
  K/R (18)
  H/R (24)
  L/V (124).

Mutation none/A (1) means that an amino-acid "A" has been added at position 1 of the sequence on portion "35L" on FIG. 11 and at position −4 of the sequence SEQ ID No 1, i.e. immediately upstream of residue No−3 if present, or if absent, immediately upstream of residue No−2, or if absent, immediately upstream of residue No−1, or if absent, immediately upstream of residue No 1.

Mutation none/I (2) means that amino-acid "I" has been added at position 2 of the sequence on portion "35L" on FIG. 11 and at position −3 of the sequence SEQ IDNo 1, i.e. immediately upstream of residue No −2 if present, or if absent, immediately upstream of residue No −1, or if absent, immediately upstream of residue No 1.

Mutation none/Q (3) means that amino-acid "Q" has been added at position 3 of the sequence on portion "35L" on FIG.

11 and at position −2 of the sequence SEQ ID No 1, i.e. immediately upstream of residue No −1 if present, or if absent, immediately upstream of residue No 1.

Mutation none/L (4) means that amino-acid "L" has been added at position 4 of the sequence on portion "35L" on FIG. 11 and at position −1 of the sequence SEQ ID No 1, i.e. immediately upstream of residue No1.

Mutation Y/S (14) means that amino-acid "Y" located at position 14 of the sequence on portion "35L" on FIG. 11 and at position 10 of the sequence SEQ ID No 1 is replaced with amino-acid "S".

Mutation K/R (18) means that amino-acid "K" located at position 18 of the sequence on portion "35L" on FIG. 11 and at position 14 of the sequence SEQ ID No 1 is replaced with amino-acid "R".

Mutation H/R (24) means that amino-acid "H" located at position 24 of the sequence on portion "35L" on FIG. 11 and at position 20 of the sequence SEQ ID No 1 is replaced with amino-acid "R".

Mutation L/V (124) means that amino-acid "L" located at position 124 of the sequence on portion "35L" on FIG. 11 and at position 100 of the sequence SEQ ID No 1 is replaced with amino-acid "V".

Preferably, the addition of at least one of these mutations enables to reduce the immunogenicity of the light-chain variable region of the IgG of the invention, as compared to that of the fragment 35PA83 from which it is derived.

Particularly advantageously, the light-chain variable region of the IgG of the invention, having an amino-acid sequence illustrated by the sequence SEQ ID No1, comprises the following mutations:
  none/A (1)
  none/I (2)
  none/Q (3)
  none/L (4).

Particularly advantageously, the light-chain variable region of the IgG of the invention, having an amino-acid sequence illustrated by the sequence SEQ ID No1, comprises the following mutations:
  none/A (1)
  none/I (2)
  none/Q (3)
  none/L (4)
  Y/S (14)
  K/R (18)
  H/R (24)
  L/V (124).

Preferably, the addition of these residues enables to reduce the immunogenicity of the light-chain variable region of the IgG of the invention, as compared to that of the fragment 35PA83 from which it is derived.

The heavy-chain variable region of the IgG of the invention (SEQ ID No 2) is derived from the variable region of the Fd fragment of the immunoglobulin fragment 35PA83, which sequence has been registered in computerized data banks, like Genbank, and is accessible under the accession numbers CAH17920 and AJ810486.

Advantageously, the heavy-chain variable region having an amino-acid sequence illustrated by the sequence SEQ ID No2 additionally comprises at least one mutation selected from:
  none/Q (1)
  none/V (2)
  none/Q (3)
  none/L (4)
  none/Q (5)
  none/E (6)
  L/V (12)
  A/T (24)
  A/T (122)
  V/L (123).

Mutation none/Q (1) means that amino-acid Q has been added at position 1 of the sequence on portion "35H" on FIG. 11 and at position −6 of the sequence SEQ ID No 2, i.e. immediately upstream of residue No−5 if present, or if absent, immediately upstream of residue No−4, or if absent, immediately upstream of residue No−3, or if absent, immediately upstream of residue No−2, or if absent, immediately upstream of residue No−1, or if absent, immediately upstream of residue No1.

Mutation none/V (2) means that amino-acid V has been added at position 2 of the sequence on portion "35H" on FIG. 11 and at position −5 of the sequence SEQ ID No 2, i.e. immediately upstream of residue No−4 if present, or if absent, immediately upstream of residue No−3, or if absent, immediately upstream of residue No−2, or if absent, immediately upstream of residue No−1, or if absent, immediately upstream of residue No1.

Mutation none/Q (3) means that amino-acid Q has been added at position 3 of the sequence on portion "35H" on FIG. 11 and at position −4 of the sequence SEQ ID No 2, i.e. immediately upstream of residue No−3 if present, or if absent, immediately upstream of residue No−2, or if absent, immediately upstream of residue No−1, or if absent, immediately upstream of residue No1.

Mutation none/L (4) means that amino-acid L has been added at position 4 of the sequence on portion "35H" on FIG. 11 and at position −3 of the sequence SEQ ID No2, i.e. immediately upstream of residue No−2 if present, or if absent, immediately upstream of residue No−1, or if absent, immediately upstream of residue No1.

Mutation none/Q (5) means that amino-acid Q has been added at position 5 of the sequence on portion "35H" on FIG. 11 and at position −2 of the sequence SEQ ID No 2, i.e. immediately upstream of residue No−1 if present, or if absent, immediately upstream of residue No1.

Mutation none/E (6) means that amino-acid E has been added at position 6 of the sequence on portion "35H" on FIG. 11 and at position −1 of the sequence SEQ ID No 2, i.e. immediately upstream of residue No1.

Mutation L/V (12) means that amino-acid L located at position 12 of the sequence on portion "35H" on FIG. 11 and at position 5 of the sequence SEQ ID No 2 is replaced with amino-acid V.

Mutation A/T (24) means that amino-acid A located at position 14 of the sequence on portion "35H" on FIG. 11 and at position 17 of the sequence SEQ ID No 2 is replaced with amino-acid T.

Mutation A/T (122) means that amino-acid A located at position 122 of the sequence on portion "35H" on FIG. 11 and at position 113 of the sequence SEQ ID No 2 is replaced with amino-acid T.

Mutation V/L (123) means that amino-acid V located at position 123 of the sequence on portion "35H" on FIG. 11 and at position 114 of the sequence SEQ ID No 2 is replaced with amino-acid L.

Preferably, the addition of at least one of these mutations enables to reduce the immunogenicity of the heavy-chain variable region of the IgG of the invention, as compared to that of the fragment 35PA83 from which it is derived.

The heavy-chain variable region of the IgG of the invention (SEQ ID No 2) is derived from the variable region of the Fd fragment of the immunoglobulin fragment 35PA83, which sequence has been registered in computerized data banks, like Genbank, and is accessible under accession numbers CAH17920 and AJ810486. The heavy-chain variable region of the invention (SEQ ID NO:2) is modified, as compared to the variable region of the immunoglobulin fragment 35PA83, in that it includes the three following mutations: G/S (31A), R/K (66) and K/R (73). Advantageously, these three mutations enable to improve the affinity of the heavy-chain variable region of the IgG according to the invention as compared to the variable region of the immunoglobulin fragment 35PA83.

Particularly advantageously, the heavy-chain variable region having an amino-acid sequence illustrated by the sequence SEQ ID No2 additionally comprises the following mutations:
none/Q (1)
none/V (2)
none/Q (3)
none/L (4)
none/Q (5)
none/E (6).

Particularly advantageously, the heavy-chain variable region having an amino-acid sequence illustrated by the sequence SEQ ID No2 additionally comprises the following mutations:
none/Q (1)
none/V (2)
none/Q (3)
none/L (4)
none/Q (5)
none/E (6)
L/V (12)
A/T (24)
A/T (122)
V/L (123).

Preferably, the addition of at least one of these mutations enables to reduce the immunogenicity of the light-chain variable region of the IgG of the invention, as compared to that of the fragment 35PA83 from which it is derived.

In a particular embodiment of the invention, the light-chain variable region of the antibody (SEQ ID NO: 1) comprises the following mutations:
none/A (1)
none/I (2)
none/Q (3)
none/L (4),
and the heavy-chain variable region of the antibody (SEQ ID NO: 2) comprises the following mutations:
none/Q (1)
none/V (2)
none/Q (3)
none/L (4)
none/Q (5)
none/E (6).

Advantageously, the light-chain constant region of the IgG of the invention comprises an amino-acid sequence comprising the sequence SEQ ID No3, and the heavy-chain constant region comprises an amino-acid sequence comprising the sequence SEQ ID No4.

For the purpose of the description of the present invention, the term "immunoglobulin" is intended to mean an immunoglobulin molecule or a fragment of an immunoglobulin molecule having the ability to specifically bind to a particular antigen. Immunoglobulin fragments, that are well known, are for example F(ab')2, Fab, Fv, scFv and Fd fragments.

Immunoglobulins of type G (IgG) are heterodimers consisting of 2 heavy chains and of 2 light chains, bound to each other through disulfide bridges. Each chain is composed, at the N-terminal position, of a variable region or domain (encoded by the rearranged genes V-J for the light chain and V-D-J for the heavy chain) specific for the antigen against which said immunoglobulin is directed, and at the C-terminal position, of a constant region, consisting of a single domain CL for the light chain or of 3 domains ($CH_1$, $CH_2$ and $CH_3$) for the heavy chain. The association of the variable domains and of the $CH_1$ and CL domains of the heavy and light chains form Fab portions, which are connected to the Fc region through a very flexible hinge region allowing each Fab to bind to its antigen target, while the Fc region, mediating the effector properties of the antibody, remains accessible to the immune effectors, phagocytes or killer cells, and the complement; these constant regions are not involved in the binding to the antigen. The Fc region, composed of the 2 globular domains, $CH_2$ and $CH_3$, is glycosylated on the $CH_2$ domain with the presence, on each of both chains, of a biantennary N-glycan of the lactosamine type, bound to Asn 297.

As concerns the variable region, it is involved in the binding of the antibody to the epitope thereof.

An antibody which constant region (Fc) has been enzymatically cleaved so as to preserve the hinge region therefrom is referred to as being a F(ab')2 fragment and retains the two antigen-binding sites.

Likewise, an antibody which constant region, including the hinge region has been enzymatically cleaved, or which has been produced without this region, is referred to as being a Fab fragment and retains one of the two antigen-binding sites.

The Fd fragment is formed of VH and $CH_1$ regions.

In the variable region are located the regions which determine the complementarity (CDRs, complementary determining regions), also called hypervariable regions, which directly interact with the antigen. Modifying the CDRs makes it thus possible to modify the affinity of an antibody. In the variable region are located regions of a second type, that are called framework regions (FRs), which maintain the tertiary structure of CDRs. These framework regions are relatively specific for the species from which the antibody is derived. In the Fd fragment of the heavy chain and in the light chain are located four framework regions (FR1 to FR4) that are respectively separated by three CDRs (CDR1 to CDR3).

According to the hereabove description of the amino-acids of the heavy-chain variable region, and of the light-chain variable region of the anti-PA IgG of the invention, the person skilled in the art is capable of synthesizing or making synthesize, nucleic acids encoding these amino-acid sequences.

Advantageously, the constant regions of each of the light chains and of the heavy chains of the IgG of the invention are human constant regions.

Preferably, the constant regions of each of the light chains of the IgG of the invention is of the κ type. Any allotype can be suitably used for implementing the invention, for example Km(1), Km(1,2), Km(1, 2, 3) or Km(3), although the preferred allotype is Km(3).

The constant region of each of the antibody heavy chains may be of the γ1 type, γ2 type or γ3 type, these three types of constant regions having the characteristic of fixing the human complement, or of the γ4 type.

Preferably, the constant region of each of the antibody heavy chains is of the γ1 type, because such an antibody is able to induce an ADCC activity in the largest number of individuals (humans). In this respect, any allotype can be suitably used for implementing the invention, for example G1m(3), G1m (1, 2, 17), G1m(1, 17) or G1m(1.3). Preferably, the allotype is G1m(1.17).

Advantageously, the constant region of each of the heavy chains of the IgG of the invention is of the γ1 type and includes the amino-acid sequence SEQ ID No4 and the constant region of each of the light chains of the IgG of the invention comprises the amino-acid sequence SEQ ID No3.

Advantageously, each of the light chains of the IgG of the invention includes the amino-acid sequence SEQ ID No5, and each of the heavy chains of the IgG of the invention comprises the amino-acid sequences of SEQ ID No6.

It is another object of the present invention to provide a nucleic acid encoding the IgG of the invention.

The variable region of each of the light chains of the IgG of the invention is encoded by the nucleic acid sequence SEQ ID NO: 7, and the variable region of each of the antibody heavy chains according to the invention is encoded by the murine nucleic acid sequence SEQ ID NO: 8.

In one particular aspect of the present invention, the constant region of each of the heavy chains of the IgG of the invention is encoded by the human nucleic acid sequence SEQ ID NO: 9, and the constant region of each of the light chain thereof being encoded by the human nucleic acid sequence SEQ ID NO: 10.

More particularly, each of the antibody light chains according to the invention is encoded by the nucleic acid sequence SEQ ID NO: 11, and each of the heavy chains is encoded by the nucleic acid sequence SEQ ID NO: 12.

It is a further object of the present invention to provide a vector comprising a nucleic acid encoding the IgG of the invention.

As used herein, a "vector" refers to a nucleic acid wherein the sequence of interest may be inserted by restriction, then ligation for the transport to and within various genetical environments or for the expression in a host cell. Vectors are for example plasmids, cosmids, yeast artificial chromosomes (YAC), bacterial artificial chromosomes (BAC) and artificial chromosomes derived from the bacteriophage P1 (PAC), virus-derived vectors. A cloning vector is a vector capable of replicating in a host cell and which in addition is characterized by the presence of one or more endonuclease restriction sites. An expression vector is a vector wherein the DNA sequence of interest may be inserted through restriction or ligation techniques so as to enable its replication and/or transcription to RNA. The vectors may contain in addition one or more markers for selecting or identifying the cells that have been transformed or transfected with the vector.

These nucleic acids can be incorporated into a recombinant vector for the cloning or for the expression of the antibodies of the invention.

The present invention includes all the recombinant vectors containing coding sequences for the purpose of eukaryotic or prokaryotic cell transformation, transfection or gene therapy. Such vectors will be prepared according to conventional methods in molecular biology and will comprise in addition a suitable promoter, optionally a signal sequence for the export or secretion, and regulatory sequences required for the transcription of the nucleotide sequence.

A fusion polypeptide may be required for purifying the antibodies of the present invention. The fusion domain may include for example a polyhistidine tail enabling the purification onto $Ni^{2+}$ columns or a filamentous phage membrane anchor, which is particularly useful for screening of a library, according to the technology called "phage display".

A vector to be suitably used in the context of the present invention is a recombinant DNA molecule adapted for receiving and expressing a first and a second DNA sequence, so as to enable the expression of heterodimer antibodies, such as a full-length antibody or F(ab')2 or Fab fragments according to the invention. Such a vector provides a system for independently cloning both DNA sequences in two separate cassettes that are present in the vector, so as to form two distinct cistrons for the expression of a first and a second polypeptide from the heterodimer antibody. Such an expression vector is called a dicistronic vector.

The modified antibodies of the present invention may be produced in eukaryotic cells such as CHO cells or human or murine hybridoma cells for example, as well as in transgenic plant and animal cells.

It is a further object of the present invention to provide prokaryotic or eukaryotic host cells, comprising a vector according to the invention.

Advantageously, the expression vector of the invention enables to express the light chain of the IgG of the invention. In this particular embodiment, the vector is a nucleic acid molecule into which the nucleic acid sequence SEQ ID NO: 7 encoding the variable region of each of the IgG light chains, and the nucleic acid sequence SEQ ID NO:10 encoding the constant region of each of the antibody light chains have been inserted, so as to introduce them into a host cell and to keep them therein. It enables the expression of these nucleic acid foreign fragments in the host cell because it does possess the required sequences (promoter, polyadenylation sequence, selection gene) for such expression. These vectors are well known from the person skilled in the art, and may be an adenovirus, a retrovirus, a plasmid or a bacteriophage, this list being non limitative. In addition, any mammal cell may be used as the host cell, that is to say as a cell expressing nucleic acid fragments carried by the expression vector of the light chain of the IgG of the invention, for example YB2/0, CHO, CHO dhfr- (for example CHO DX B11, CHO DG44), CHO Lec13, SP2/0, NS0, 293, BHK or COS.

Advantageously, the expression vector of the invention enables to express the heavy chain of the IgG of the invention. In this particular embodiment, the vector is a molecule enabling the expression of the IgG of the invention, the heavy chain of which is encoded by the nucleic acid sequence SED ID NO: 12. This vector is a nucleic acid molecule into which the nucleic acid sequence SEQ ID NO: 8 encoding the variable region of each of the IgG heavy chains, and the nucleic acid sequence SEQ ID NO: 9 encoding the constant region of each of the antibody heavy chains have been inserted, so as to introduce them into a host cell and to keep them therein. It enables the expression of these nucleic acid foreign fragments in the host cell because it does possess the required sequences (promoter, polyadenylation sequence, selection gene) for such expression. As previously stated, the vector may be for example a plasmid, an adenovirus, a retrovirus or a bacteriophage, and the host cell may be any mammal cell, for example YB2/0, CHO, CHO dhfr- (CHO DX B11, CHO DG44), CHO Lec13, SP2/0, NS0, 293, BHK or COS.

The vector of the invention may include the sequences encoding the heavy chain and/or the light chains of the immunoglobulin of the invention.

An example of a vector enabling the expression of the heavy and light chains of the IgG of the invention is given in Example 2. This vector is a unique vector containing the two transcription units for the heavy chain and for the light chain of the IgG of the invention.

It is another object of the present invention to provide a host cell comprising the vector such as defined hereabove.

Advantageously, the host cell of the invention is selected from SP2/0, YB2/0, IR983F, Namalwa human myeloma, PERC6, CHO cell lines, in particular CHO-K-1, CHO-Lec10, CHO-Lec1, CHO-Lec13, CHO Pro-5, CHO dhfr-, Wil-2, Jurkat, Vero, Molt-4, COS-7, 293-HEK, BHK, K6H6, NS0, SP2/0-Ag 14 and P3X63Ag8.653.

In a preferred embodiment, the antibody is produced in YB2/0 rat hybridoma (YB2/3HL.P2.G11.16Ag.20 cell, filed in the American Type Culture Collection under accession number ATCC CRL-1662). This cell line was chosen because of its ability to produce antibodies having an ADCC activity (antibody-dependent cell-mediated cytotoxicity) that was improved as compared with antibodies of similar primary structure obtained for example in CHO cells.

In one particular aspect of the present invention, the stable cell line expressing an antibody of the invention, and more particularly selected from the previously described group, did integrate one or both expression vector(s) of the heavy chain and of the light chain such as previously described.

It is a further object of the present invention to provide a composition comprising at least one IgG of the invention.

It is a further object of the present invention to provide a pharmaceutical composition comprising at least one IgG of the invention.

Said pharmaceutical composition preferably includes a pharmaceutically acceptable vehicle. Such a vehicle as used herein is intended to mean a non toxic material which does not interfere with the biological activity efficiency of the active components of the composition. The expression "pharmaceutically acceptable" does refer to a non toxic material which is compatible with a biological system such as a cell, a cell culture, a tissue or an organism. The vehicle characteristics will depend on the method of administration.

The present invention relates to the use of at least one IgG of the invention for the preparation of a pharmaceutical composition or a medication for treating or preventing an infection with *Bacillus anthracis*.

As used herein, the term "prevention" means to prevent the occurrence of the disease in a subject, particularly a human, in whom the disease has not yet appeared.

As used herein, the term "treatment" corresponds to the inhibition of this disease, i.e. the discontinuation of its development, its regression, or the disappearance of the symptoms and consequences of the disease, or the disappearance of the causes of the disease.

The IgG of the invention may be labeled. Examples of suitable markers include enzymes, radioisotopes, fluorescent compounds, colloidal metals, chimioluminescent compounds, and bioluminescent compounds.

The binding methods of a marker to an antibody are well known from the person skilled in the art.

Another labeling method consists in coupling the antibody to low-molecular weight haptens, which haptens may be specifically modified through a second reaction. Examples of suitable haptens include biotin, which reacts with avidin, or dinitrophenol, pyridoxal or fluorescein, which may react with anti-hapten specific antibodies.

It is an object of the present invention to provide a PA-containing anthrax toxin detection kit. This kit comprises:
a container comprising at least one anti-PA IgG of the invention and which may be labeled or not,
optionally, a container comprising buffer solutions,
and optionally a container comprising labeled IgG detecting means, such as a biotin-binding protein, for example avidin or streptavidine, bound to a reporter molecule, such as a fluorescent or enzymatic marker. This container may also comprise non-labeled IgG detecting means, i.e. substantially antibodies or antibody fragments.

The IgG of the invention may be used in vitro, for example in immunological assays wherein they are used in a liquid phase or immobilized on a solid-phase vehicle. Examples of well known vehicles include glass, polystyrene, polypropylene, polyethylene, dextran, nylon, amylase, natural or modified cellulose, polyacrylamide, agarose or magnetite. Examples of immunological assays using the anti-PA IgG of the invention are radioimmunoassays, histoimmunological labeling techniques, ELISAs, Western blots, immunoprecipitation assays, immunodiffusion assays, complement fixation assays, Fluorescence-activated Cell Sorting assays (FACS) or protein-chip analyses.

It is a further object of the present invention to provide a method for detecting in vitro a PA-containing anthrax toxin, in a biological sample, comprising the steps of:
contacting the sample with at least one anti-PA IgG of the invention, and
detecting the binding of said antibody as an indication of the presence of said anthrax toxin.

The biological sample may be liquid: for example saliva, urine, cerebrospinal fluid, serum or blood, or solid or semi-solid, for example tissues or feces or a solid tissue such as traditionally used in histological diagnosis.

It is a further object of the present invention to provide a method for detecting in vivo a PA-containing anthrax toxin, wherein a labeled IgG of the invention is administered to a subject. The administered amount of labeled IgG should be sufficient for the binding of the antibody to the toxin to be detected. The administered amount of labeled IgG will depend on some factors such as the age and sex of the subject, as well as on the stage of the disease. The administered amount may vary from 0.01 mg/kg to 50 mg/kg, preferably from 0.1 mg/kg to 20 mg/kg, and more preferably from 0.1 mg/kg to 2 mg/kg.

To perform the in vivo diagnosis, the modified anti-PA IgG of the invention should be linked to a radioisotope, either directly or indirectly, through functional groups. Commonly used functional groups include for example diethylene-tri-amine-pentacetic acid (DTPA) and ethylene-diamine-tetraacetic acid (EDTA). Examples of radioisotope metal ions include $^{111}$In, $^{97}$Ru, $^{67}$Ga, $^{68}$Ga, $^{72}$As, $^{89}$Zr and $^{201}$Tl.

The modified anti-PA IgGs of the invention may also be labeled with a paramagnetic isotope for a diagnosis using the magnetic resonance imaging (MRI) or through electron spin resonance (ESR). Positron-emitting gamma radioisotopes may also be used, such as $^{157}$Gd, $^{55}$Mn, $^{162}$Dy, $^{68}$Ga, $^{52}$Cr, and $^{56}$Fe.

The IgGs of the invention may also be used in vitro or in vivo for monitoring the evolution of the treatment of the disease, for example by determining the increase or the decrease in the number of cells targeted by anthrax toxins or the change in the PA toxin concentration in a biological sample.

It is an object of the present invention to provide a method for treating a subject, preferably a human, potentially infected with *Bacillus anthracis*, wherein a therapeutically efficient amount of an anti-PA antibody modified according to the invention is administered to said subject.

As used herein, the expression "therapeutically efficient amount" is intended to mean the amount which is sufficient for performing the treatment when administered to a subject which is in need of such a treatment. The therapeutic effective amount depends on the subject, on the stage of the disease to treat and on the method of administration, and may be determined through routine procedures by the person skilled in the art.

As used herein, the term "anthrax" is intended to mean any disease caused, either directly or indirectly, by an infection with *Bacillus anthracis*. Initial symptoms of an inhalational infection are similar to those of coryza (fever, muscular pain . . . ). After a couple of days, these symptoms evolve towards serious problems of respiratory distress and septic shock. Inhalating the bacteria anthrax is usually fatal.

Anthrax cutaneous infection occurs when the bacterium penetrates into the skin through a preexisting cutaneous interstice. This infection does initially cause the formation of a papule, which develops within two or three days to a vesicle, thereafter to a 1 to 3 cm-diameter ulceration with a central necrotic area. The anthrax gastrointestinal infection results from the consumption of contaminated meat and is characterized by an acute inflammation of the intestinal tract.

A therapeutically efficient amount corresponds to an amount that is sufficient for reducing the symptoms of the disease and the infection evolution. Such amount may vary depending on the age and sex of the subject and on the stage of the disease and will be determined by the person skilled in the art. A therapeutically efficient amount may vary from 0.01 mg/kg to 50 mg/kg, preferably from 0.1 mg/kg to 20 mg/kg, and more preferably from 0.1 mg/kg to 2 mg/kg, in one or several doses per day, for one day, or longer.

The administration method may be injection or gradual infusion. Injection may be of the intravenous, intraperitoneal, intramuscular, subcutaneous or transdermal type.

Preparations for parenteral administration may include sterile aqueous or non-aqueous solutions, suspensions or emulsions. Examples of non-aqueous solvents include propylene glycol, polyethylene glycol, vegetable oils, such as olive oil, or injectable organic esters, such as ethyl oleate. Aqueous vehicles include water, alcohol/water solutions, emulsions or suspensions.

It is a further object of the present invention to provide an immunoconjugate comprising the IgG of the invention associated, either directly or indirectly, with a therapeutic agent.

Such therapeutic agents include chemical agents, radionuclides, immunotherapeutic agents, cytokines, chemokines, toxins or enzyme inhibitors. To be mentioned as examples of toxins are the diphtheria-toxin chain A, the exotoxin chain A, the ricin chain A, the abrine chain A, the modeccin chain A, alpha-sarcin, Aleurite fordii proteins, dianthin proteins, Phytolaca americana proteins, momordica charantia inhibitor, curcin, crotin, sapaonaria officinalis inhibitor, gelonine, mitogelline, restrictocine, phenomycine, enomycine and tricothecenes. Radionuclide examples include $^{212}Bi$, $^{131}I$, $^{131}In$, $^{90}Y$, and $^{186}Re$.

Advantageously, the IgG of the invention is associated with a tetracycline-based prophylactic treatment. The IgG of the invention enables to shorten the tetracycline-based prophylaxis, by stopping, in a secured manner, after an exposure risk, through a tetracycline-based quick treatment ("short treatment") followed with an injection of the IgG of the invention.

Advantageously, the IgG of the invention is associated with a curative treatment with ciprofloxacin.

The present invention will be more easily understood using the following description supplement, referring to anti-PA IgG preparation examples.

DESCRIPTION OF THE FIGURES

In the following examples, given as an illustration, it will be referred to the appended figures hereunder:

FIG. 7: Prophylactic treatment with doxycycline, complemented or not with IgG 35PA83. A tetracycline-based treatment (daily dose of 5 mg/kg) was initiated in A/J mice. After twelve hours, the animals were infected with 10 000 $LD_{50}$ of Sterne strain spores. Tetracycline injections were stopped on day 7 of the treatment, in the presence or in the absence of an injection of 35PA83 (1 or 2 mg/kg). No special event could be observed beyond the time period illustrated on the figure ($500^{th}$ hour). Highly significant effects are indicated on the figure with sign "***".

The IMGT pearl-on-a-string configuration is in accordance with IMGT nomenclature. Points indicate the differences in human genes that are the most similar to 35PA83, and 35PA83. Hatched circles correspond to the missing positions in accordance with IMGT nomenclature.

EXAMPLES

Example 1

Construction of Fab (35PA83) Mutant Library

Materials and Methods
E. coli Strains
Following E. coli strains were used:
XL1 (Stratagène, the jolla, CA): recA1, endA1, gyrA96 thi-1 hsdR17 sup E44 relA1 lac [F'proAB laclqZΔM15 Tn10(Tetr)].

SURE (Stratagène): e14(McrA) Δ(mcrCB-hsdSMR-mrr) 171 endA1 supE44 thi-1 gyrA96 relA1 lac recB recJ sbcC umuC::Tn5 (Kanr) uvrC [F' proAB laclqZΔM15 Tn10 (Tetr)]

HB2151 (Carte and al., 1985), used for the expression of soluble Fabs.

Toxins

Anthrax toxins (PA83, LF and EF) acquired from List laboratories.

Construction of the 35PA83 Mutant Library

A mutant of the immunoglobulin fragment 35PA83 was constructed to be humanized. This mutant has been obtained by performing the mutations described in Tables 3 and 4:

TABLE 1

Mutations for humanizing 35PA83 light chain

| Residue number | 35PA83 | Hu35PA83 |
|---|---|---|
| 1 | None | A |
| 2 | None | I |
| 3 | None | Q |
| 4 | None | L |

TABLE 2

Mutations for humanizing 35PA83 Fd

| Residue number | 35PA83 | Hu35PA83 |
|---|---|---|
| 1 | None | Q |
| 2 | None | V |
| 3 | None | Q |
| 4 | None | L |
| 5 | None | Q |
| 6 | None | E |

Starting from this humanized mutant, a mutant antibody library derived from gene 35PA83 was generated by Massive mutagenesis® (Biomethods, Evry, France). Mutations were introduced into the CDRs of the heavy and light chains by using NNS codons (N encodes A, T, G, or C and S encodes G or C). CDR regions were defined according to Kabat and al. (Wu and Kabat 1970) and IMGT (Lefranc, Pommie and al. 2003).

The DNA library was used for transforming SURE cells by electroporation. After adding carbenicillin-supplemented SB medium to the culture and incubation for 1 h at 37° C., 1 ml of phage helper VCSM13 (Andris-Widhopf and al., 2001) (approx. 1012 pfu) has been added to the culture. After incubation for 2h, 70 μg/ml of kanamycin were added and the culture was placed under stirring for one night at 37° C.

Selection of Antibodies by Phage Display

Phage-Fab particles were purified and concentrated from 50 ml of culture by precipitation with PEG, then re-suspended in 3 ml of 1% PBS-BSA −0.02% azide and filtered on a 0.45 μm-filter. The titer of this phage preparation was of about 1010 pfu/ml. Phage-Fabs were submitted to three infection-selection recovery cycles, corresponding to 5, 10 and 15 washings respectively, such as previously described (Andris-Widhopf, Rader and al. 2000).

Expression of Soluble Fab, Periplasmic Extraction and Purification

Each DNA mutant was transformed in bacteria of the *E. coli* strain called HB2151, made chemically competent. The cells were cultured at 30° C., stirred at 250 rpm in 1L of SB medium containing 50 μg/ml of carbenicilline and 0.1% glucose. When the culture had reached absorbance of 1.5 at λ=600 nm, induction with 1 mM IPTG (Isopropyl β-D-1-thiogalactopyranoside) was performed for 18 h at 22° C.

Fabs were extracted with polymixine B sulphate (Sigma) and purified on a nickel column (Ni-NTA spin column, QIAGEN, Valencia, Calif.) according to the supplier's instructions, then dialyzed with PBS 1× at 4° C. for 3 h.

Quantification of Soluble Fabs

The Fab purity was tested through SDS-PAGE and the concentration thereof determined using the software Quantity One® (Biorad).

Measurement in Real Time of the Surface Plasmon Resonance (SPR)

The kinetic constants for the interaction between PA83 and 35PA83 mutants were determined by using system Biacore× SPR (BIAcore, Uppsala, Sweden). PA83 was immobilized onto a CM5 sensitive chip (Biacore) by using an amine coupling procedure by injecting 30 μl for 2 μg/ml of PA83 in 10 mM sodium acetate pH 4.5. For minimizing the probability of rebinding, KD was measured by using a high flow rate (30 μl/min) and a minimum amount of coupled antigen (approx. 500 RU, resonance units). The binding ratio for Fab with various concentrations ranging from 5 to 400 nM in PBS was determined with a flow rate of 30 μl/min. Binding data were introduced into a 1:1 model of Langmuir of the BIA evaluation software (Biacore). Association and dissociation constants ($k_{on}$ and $k_{off}$ respectively) for the binding of Fab to PA83 were determined at 35° C.

Analysis of the Sequences

The heavy and light chain sequences of the selected clones were determined through Genome Express sequencing (Meylan, France) by using ompseq and newpelseq primers (Andris-Widhopf, Rader and al., 2000). The sequences were analyzed online, by using the IMGT system (http:/imgt.cines.fr).

Results

An in vitro affinity maturation was carried out to generate new mutants with an improved affinity. To this purpose, a mutant library was created by exclusively mutating residues from 6 CDRs, that is to say residues located at 73 positions. Concerning the size, the library contained $5.4.10^8$ transformants. 45 independent plasmid clones were sequenced for determining the diversity and the mutation rate. The experimental mutation rate corresponds to 3 mutations/fragment (VH+VL), which makes it possible to directly select mutation combinations improving the affinity for PA.

Analyzing the mutation frequency at each position in the target CDR in the non-selected library as compared to the selected library (Table 1) revealed that some positions do not tolerate the variation. Thus, residues located at these positions seem to be key residues for the binding to the antigen, preserving the antigen-binding site integrity. Particularly, (H31-H40) residues in CDR1 are defined as antigen-contacting residues.

It seems as if a substantial selection pressure was exerted during the selection process, as the non-selected library has a broader diversity as compared to the selected sequences, particularly in L-CDR1 and H-CDR1.

Amongst all mutated positions, a combination of mutations showed a markedly improved affinity: clone v2, the binding affinity and kinetics of which are given in Table 3.

TABLE 3

Binding affinity and kinetics for Fab 35PA83 and clone v2.

| Parental clone | Sequence H | Sequence L | KD (M) | Kon (M-1 · s-1) | Koff (s-1) |
|---|---|---|---|---|---|
| 35PA83 | parental type | parental type | $3.4 \cdot 10^{-9}$ | $9.3 \cdot 10^{4}$ | $3.2 \cdot 10^{-4}$ |
| Clone v2 | G > S (31A) R > K (66) K > R (73) | parental type | $6.6 \cdot 10^{-10}$ | $1.22 \cdot 10^{5}$ | $8.1 \cdot 10^{-5}$ |

Association ($k_{on}$) and dissociation ($k_{off}$) constants were determined through surface plasmon resonance (BIAcore) and $K_D$ was calculated as corresponding to the $K_{off}/K_{on}$ ratio.

V2 triple mutant showed a lower dissociation constant ($K_{off}$=8.1 $10^5$ s-1) and an association constant a little faster ($K_{on}$=1.22 $10^5$ M-1.s-1) than 35PA83, thus multiplying the affinity×5.15. This mutant contains 3 mutations in the heavy chain variable domain: one mutation (G31AS) in H-CDR1 (CDR1 of the heavy-chain variable region) and two mutations (R66K, K73R) in H-CDR2 (CDR2 of the heavy-chain variable region).

After the third cycle, the phages were screened according to two additional selection methods: panning in antigen-covered wells with a long-lasting incubation ("long-lasting incubation selection") or using a soluble, biotinylated antigen at a very low concentration ("very low concentration soluble antigen selection").

Example 2

Construction of Expression Vector HK558-12 for the Expression of Cynomolgus-Human Chimera IqG 35PA83 v2

The heavy-chain variable region (VH) of the selected mutant (v2) contains three mutations as compared to the humanized mutant of Fab 35PA83: G→>S ($6^{th}$ residue of HI, according to the IMGT nomenclature), →R>K ($2^{d}$ anchoring residue of H2) and K→>R ($6^{th}$ residue of FR3 according to the IMGT nomenclature).

Figure 3:
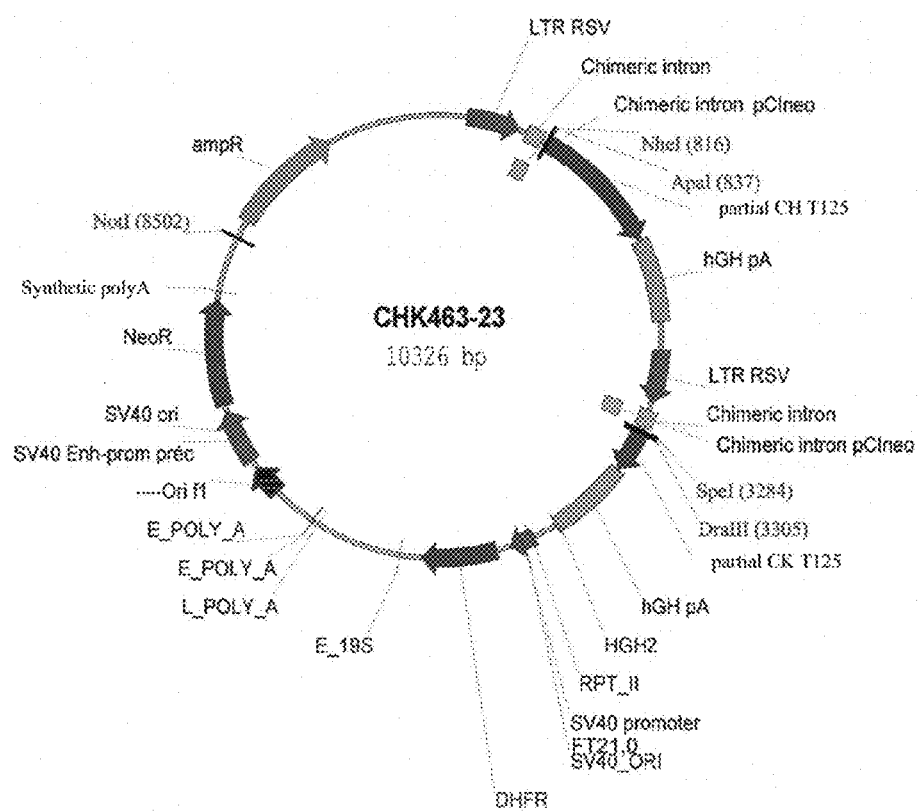
FIG. 3: map of vector CHK463-23.
Figure 4:
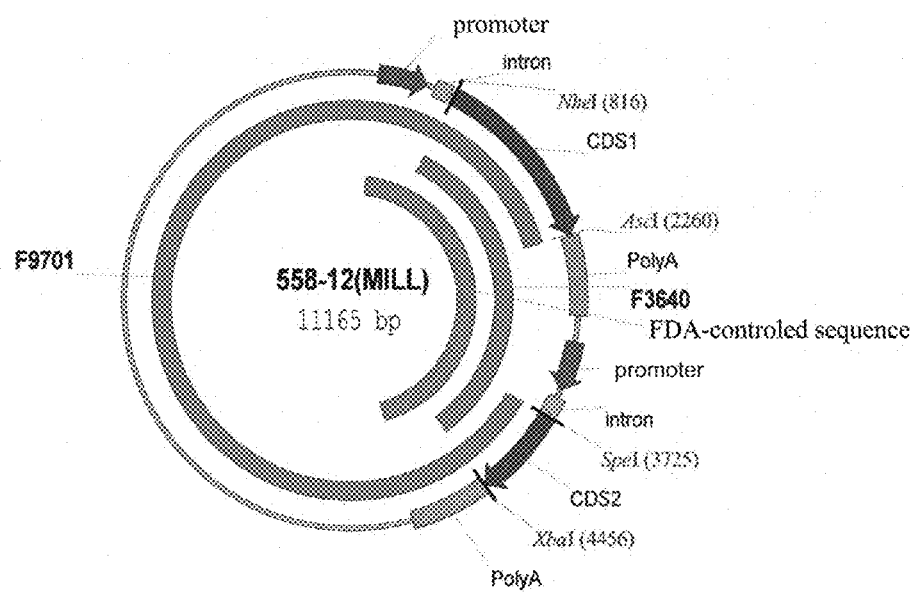
FIG. 4: map of vector HK558-12.
Figure 5:
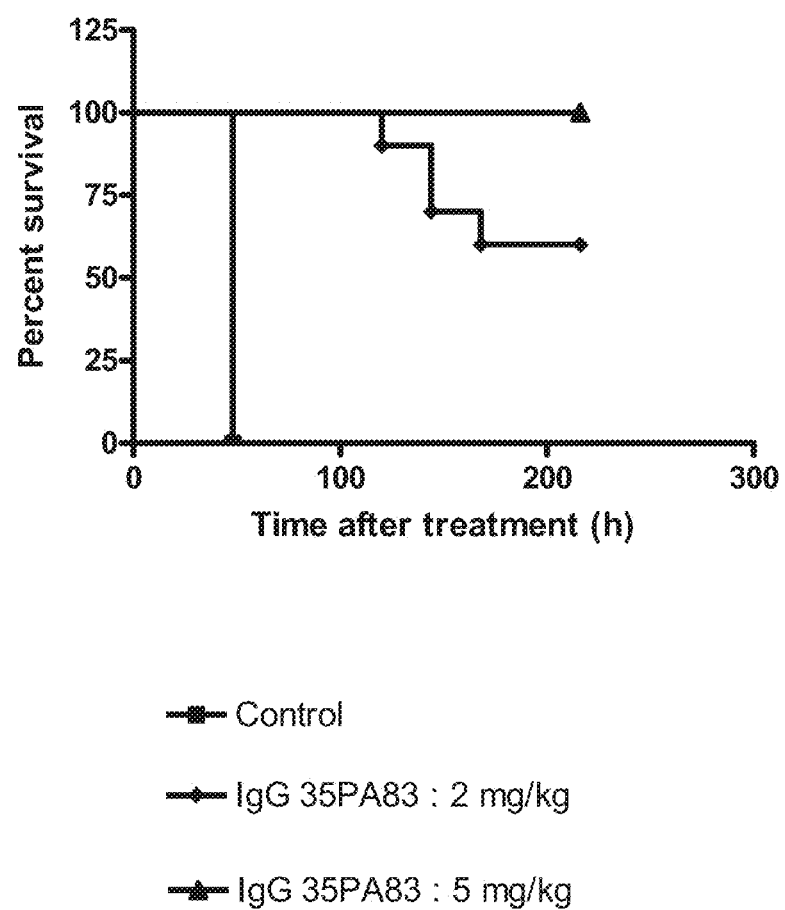
FIG. 5: prophylactic treatment with IgG 35PA83 v2 (the IgG of the invention including mutations described in Tables 1 and 2). 2 mg/kg of IgG 35PA83 v2 enable to obtain a survival rate of 60% and 5 mg/kg enable to obtain a 100% survival. No new event could be observed until day 30.
Figure 6:
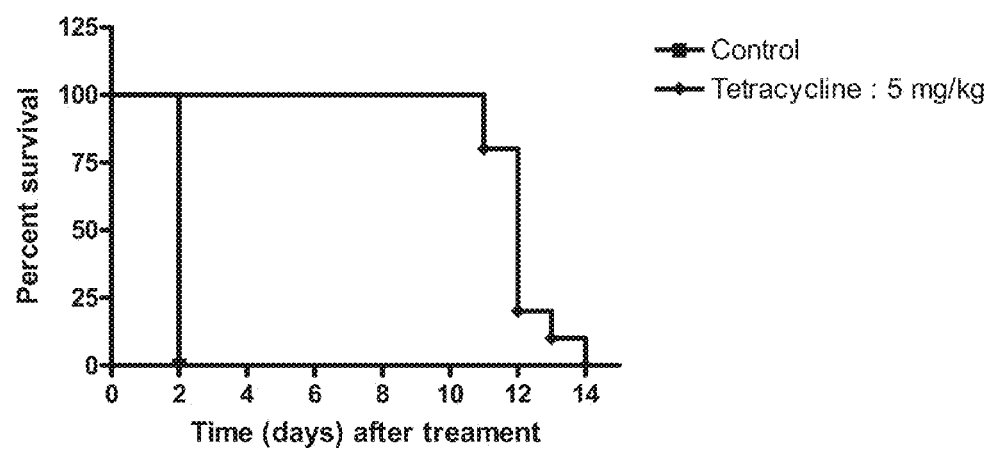
FIG. 6: prophylactic treatment with tetracycline. The tetracycline administration was discontinued after day 7 and all the mice died between the $4^{th}$ and the $7^{th}$ day following this treatment discontinuation.

Vector HK558-12 (see FIG. 4) was constructed from the optimized unique generic vector CHK463-23-1 (see FIG. 3) through a "double" chimerization, that is to say by adding to the cynomolgus v2 sequence human leader regions in 5' (v2 cloned sequences in plasmid pCOMB (Andris-Widhopf and al., 2000) do not contain the leader sequences), and human constant regions CK and G1 in 3'.

1. Principle of the Methods

Molecular biology traditional techniques have been implemented for the construction of vector HK558-12. DNA sequences of interest have been amplified through assembly PCR (10 cycles with enzyme "Proofstart DNA polymerase" Qiagen ref. 202 203) and cloned (digestion through a restriction enzyme, then ligation) in a plasmid or an expression vector. The thus obtained recombinant plasmids thereafter have been introduced into bacteria (transformation of bacteria) for amplification (culture of bacteria) so as to produce vectors in sufficient amounts for the transfection step. The vectors obtained during the bacteria culture process have then been purified, thereafter linearized in expectation of the transfection in YB2/0 and CHO cell lines.

1.1 Synthesis Via Assembly PCR of the Light-Chain Variable Region of the Mutant v2 (VKv2)

Region VKv2 corresponds to the chimerization of following regions:

leader of the light-chain variable region (VK)-start VK: human sequence Z0006(Accession Number) (subgroup VK1,VK1-13), choice CRSSA-IMGT:

VK cynomolgus (plasmid pComb3X, described in the article of Laffly and al., 2005, which contains VH and VL sequences of v2).

The human leader sequence is added in 5' of the VK cynomolgus to give following sequence:

(SEQ ID N° 13)
ATGGACATGAGGGTCCCCGCTCAGCTCCTGGGGCTTCTGCTGCTCTG

GCTCCCAGGTGCCAGATGT*GCCATCCAGTTG*
(in italics: start human VK)

This sequence does not contain any of the restriction sites used for cloning procedures.

Amplification of region VKv2:
Primer Pair VK1_CA and VK2_CA

VK1_CA:
(SEQ ID N° 14)
5'-*CTCAGTACTAGTGCCGCCACC*ATGGACATGAGGGTCCCCGCTC
AGCT-3'

VK2_CA:
(SEQ ID N° 15)
5'-ACCTGGGAGCCAGAGCAGCAGAAGCCCCAGGAGCTGAGCGGGG
A-3'

This primer pair enables the introduction of site Spe I and the start of the leader sequence corresponding to human VK leader (VK1-13 Z00006, Accession Number) the most similar to the sequence of v2.

The obtained amplicon corresponds to amplicon 1 (78 pb).

Primer pair VK3_CA and VK4_CA

VK3_CA:
(SEQ ID N° 16)
5'-*TGCTCTGGCTCCCAGGTGCCAGATGTGCCATCCAGTTG*ACCCA-3'

VK4_CA:
(SEQ ID N° 17)
5'-CTCCCACATATGCAGACAGGGACGATGGAGACTGGGTCAACTGGA-3'

This primer pair enables to introduce the remaining leader sequence i.e. the region 5' of the human VK (VK1-13 Z00006) and the start of the VK of v2. The obtained amplicon corresponds to amplicon 2 (75 pb).

Primer pair VK1_CA and VK4_CA

VK1_CA:
(SEQ ID N° 18)
5'-*CTCAGTACTAGTGCCGCCACC*ATGGACATGAGGGTCCCCGCTCA
GCT-3'

-continued

VK4_CA:
(SEQ ID N° 19)
5'-CTCCCACATATGCAGACAGGGACGATGGAGACTGGGTCAACTGGA-3'

This primer pair enables to obtain amplicon 3 (136 pb) via assembly PCR of amplicons 1 and 2.

Primer pair VK_CA_Nde and VK_CA_Dra

VK_CA_Nde:
(SEQ ID N° 20)
5'-TCGTCCCTGTCTGCATATGTGGGAG-3'

VK_CA_Dra:
(SEQ ID N° 21)
5'-GATGAAGACACTTGGTGCAGCCACAGTTCGTTTGATATCCAG-3'

This primer pair enables to obtain amplicon 4 (327 pb) by using as a template plasmid pCOMB v2. In addition, amplicon 4 contains upstream the human region VK enabling the last assembly PCR with amplicon 3.

Primer Pair VK1_CA and VK_CA_Dra

VK1_CA:
(SEQ ID N° 22)
5'-CTCAGTACTAGTGCCGCCACCATGGACATGAGGGTCCCCGCTCAGCT-3'

VK_CA_Dra:
(SEQ ID N° 23)
5'-GATGAAGACACTTGGTGCAGCCACAGTTCGTTTGATATCCAG-3'

This primer pair enables to obtain amplicon 5 (438 pb) via assembly PCR of amplicons 3 and 4. It enables the human leader sequence VK and VK cynomolgus sequence concatenation.

Figure 1:
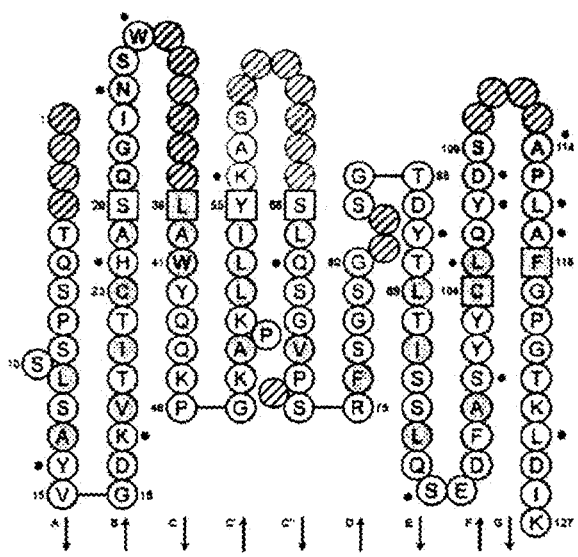
FIG. 1: amplification diagram of region VKV2 (variable region of the light chain of the IgG of the invention including mutations described in Table 1).
Figure 1:
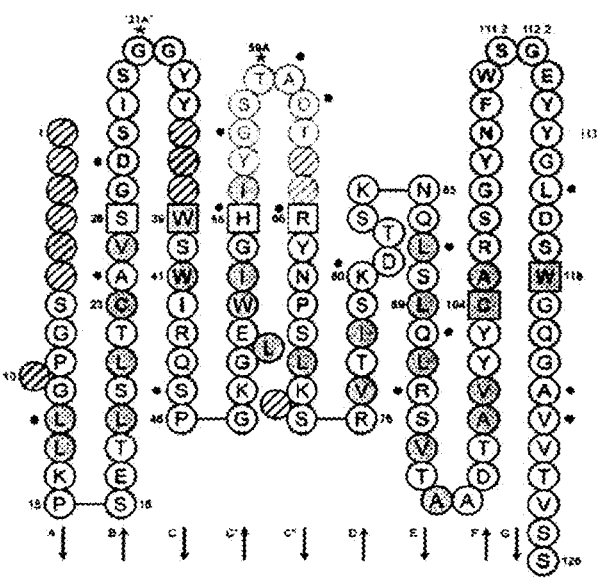
Figure 1:
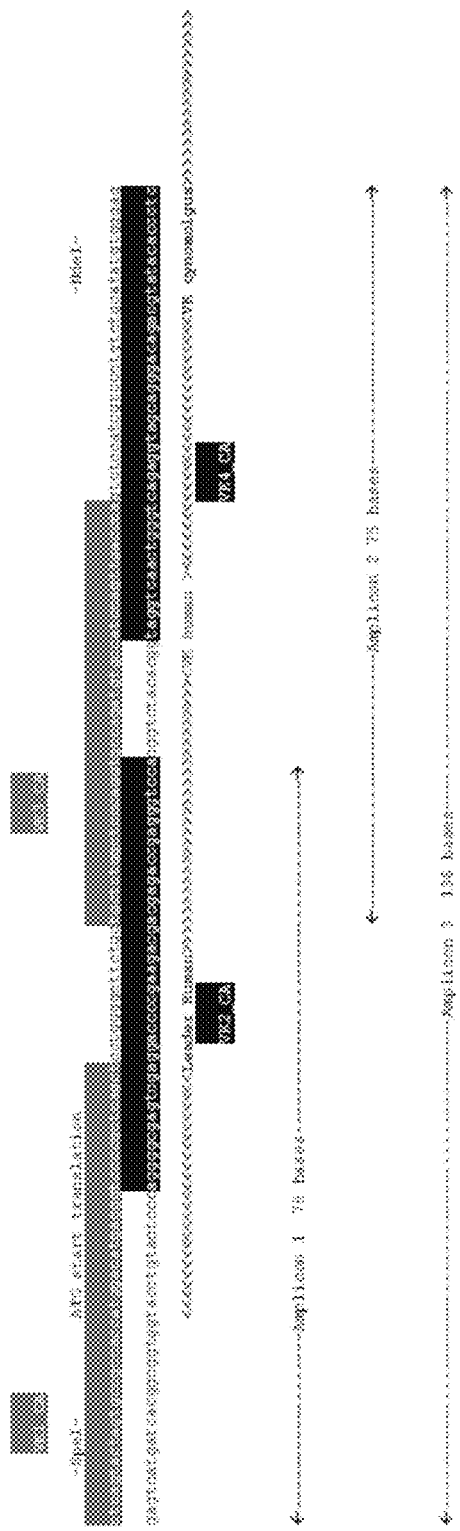
Figure 1:
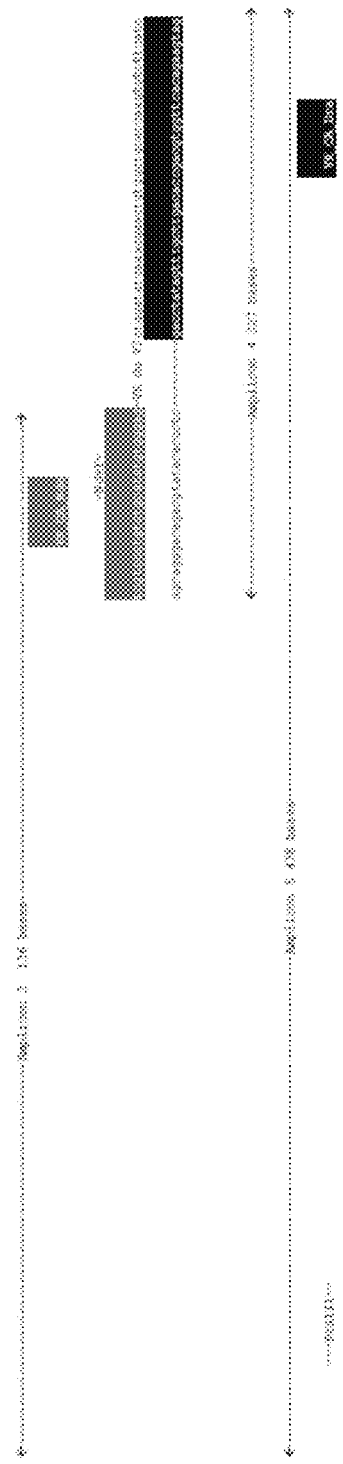

The resulting primer and amplicon sequences are illustrated on FIG. 1.

Amplicon 3 is obtained via assembly PCR of amplicons 1 and 2 introducing site Spe I, human leader sequence VKe and the start of the sequence VK of v2. Amplicon 4 corresponds to the VK coding sequence of v2.

Final amplicon 5 is obtained via assembly PCR of amplicons 3 and 4 for enabling the concatenation of human VK leader sequences and VK cynomolgus sequences.

1.2 Synthesis Via Assembly PCR of the Heavy-Chain Variable Region with Mutant v2 (VHV2)

Region VHv2 corresponds to the chimerization of following regions:
 leader VH-start VH: human sequence M29812 (Accession Number) (subgroup VH4,VH4-59). Human genes V encoding the sequences that are the most similar to 35PA83: IGHV4-59*01 for Fd and IGKV1-13*02 for the light chain (IMGT nomenclature), mutated as described hereabove
 cynomolgus VH (plasmid pComb3X)

The human sequence is added in 5' of the cynomolgus VH to give following sequence:

(SEQ ID N° 24)
ATGAAACATCTGTGGTTCTTCCTTCTCCTGGTGGCAGCTCCCAGATGG
GTCCTGTCC*CAGGTGCAGCTGCAGGAGT*
(in italics: start human VH)

This sequence does not contain any of the restriction sites used for cloning procedures.

Figure 2:
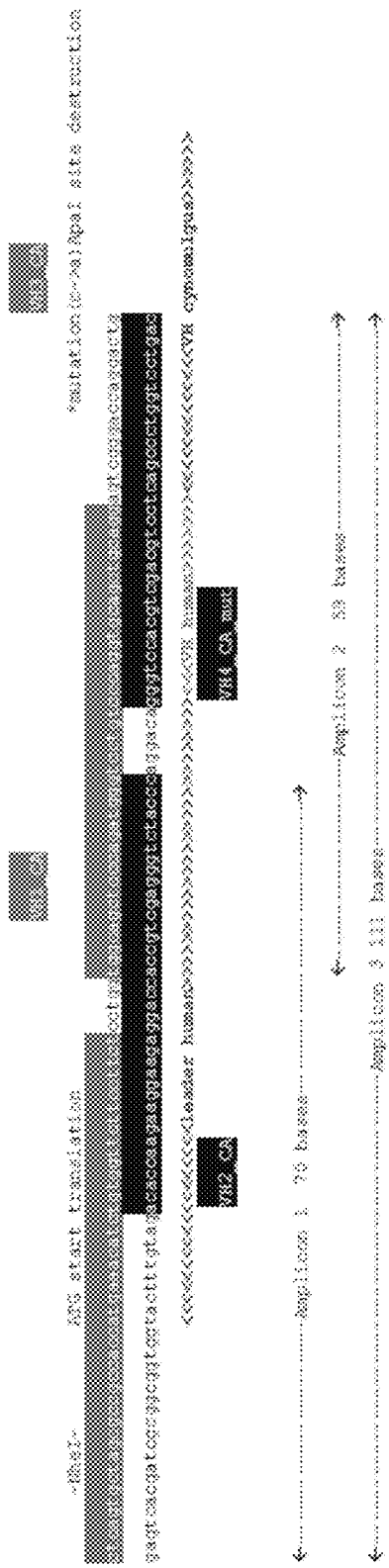
FIG. 2: amplification diagram of region VHV2 (heavy-chain variable region of the IgG of the invention including mutations described in Table 2).
Figure 2:
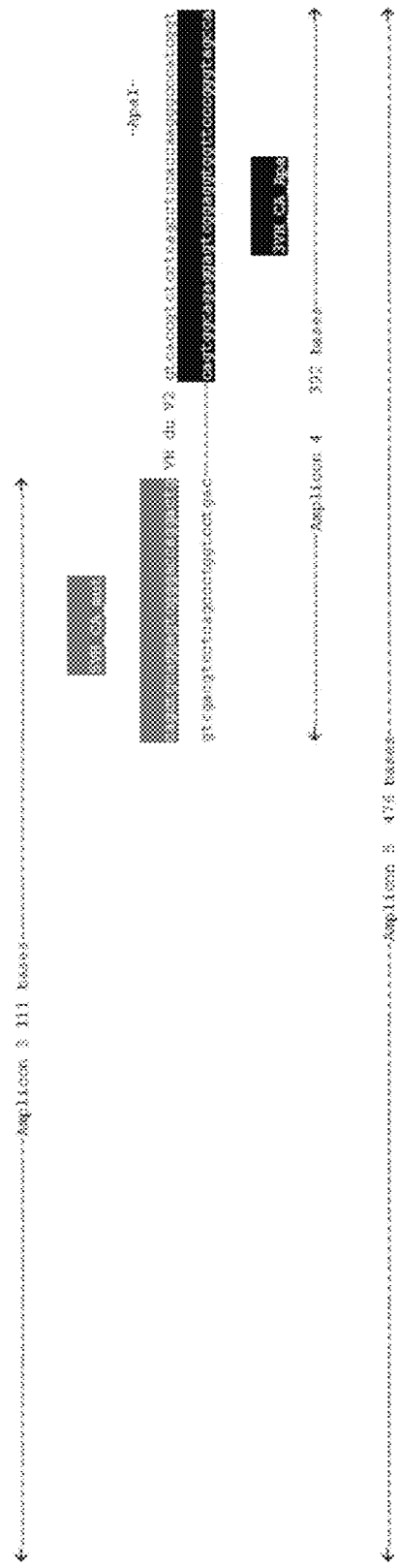

FIG. 2 shows the synthesis of region VHV2 with the various primer pairs and amplicons obtained.

1.2.1 Amplification of Region VHV2

Amplification of region VHV2 is illustrated on FIG. 2.

Primer Pair VH1_CA and VH2_CA

VH1_CA:
(SEQ ID N° 25)
5'-CTCAGTGCTAGCGCCGCCACCATGAAACATCTGTGGTTCTTCCTTCT-3'

VH2_CA:
(SEQ ID N° 26)
5'-CCCATCTGGGAGCTGCCACCAGGAGAAGGAAGAACCACA-3'

This primer pair enables the introduction of site Nhe I and the start of the leader sequence corresponding to leader human VH (VH4-59 M29812, human genes V encoding the sequences that are the most similar to 35PA83: IGHV4-59*01 for Fd and IGKV1-13*02 for the light chain (IMGT nomenclature), mutated as described hereabove) the most similar to the sequence of v2. The obtained amplicon corresponds to amplicon 1 (70 pb).

primer Pair VH3_CA and VH4_CA_mut

VH3_CA:
(SEQ ID N° 27)
5'-TGGCAGCTCCCAGATGGGTCCTGTCCCAGGTGCAGCTGCAGG-3'

VH4_CA_mut:
(SEQ ID N° 28)
5'-CAGTCCTGGTCCCGACTCCTGCAGCTGCACCTGGG-3'

This primer pair enables to introduce the remaining leader sequence i.e. the region 5' of the human VH (VH4 M29812) and the start of the sequence VH of v2. Primer VH4_CA deletes via mutagenesis site Apa I at the start of the VH. The obtained amplicon corresponds to amplicon 2 (59 pb).

Primer Pair VH1_CA and VH4_CA_mut

VH1_CA:
(SEQ ID N° 29)
5'-CTCAGTGCTAGCGCCGCCACCATGAAACATCTGTGGTTCTTCCTTCT-3'

VH4_CA_mut:
(SEQ ID N° 30)
5'-CAGTCCTGGTCCCGACTCCTGCAGCTGCACCTGGG-3'

This primer pair enables to obtain amplicon 3 (111 pb) via assembly PCR of amplicons 1 and 2.

Primer Pair 5VH_CA_mut and 3VH_CA_Apa

5VH_CA_mut:
(SEQ ID N° 31)
5'-CAGCTGCAGGAGTCGGGACCAGGACTG-3'

3VH_CA_Apa:
(SEQ ID N° 32)
5'-ACCGATGGGCCCTTGGTGGAGGCTGAGGAGACGGTGAC-3'

This primer pair enables to obtain amplicon 4 (392 bases) by using as a template plasmid pCOMB V2. In addition, amplicon 4 contains upstream the human region VH enabling the last assembly PCR.

Primer Pair VH1_CA and 3VH_CA_Apa

VH1_CA:
(SEQ ID N° 33)
5'-CTCAGTGCTAGCGCCGCCACCATGAAACATCTGTGGTTCTTCCT
TCT-3'

3VH_CA_Apa:
(SEQ ID N° 34)
5'-ACCGATGGGCCCTTGGTGGAGGCTGAGGAGACGGTGAC-3'

This primer pair enables to obtain amplicon 5 (476 pb) via assembly PCR of amplicons 3 and 4. It enables the concatenation of the human VH and cynomolgus VH leader sequences.

The resulting primer and amplicon sequences are illustrated on FIG. 2.

Amplicon 3 is obtained via assembly PCR of amplicons 1 and 2 introducing site Nhe I, human VH leader sequence and the start of the sequence VH of v2. Amplicon 4 corresponds to the VH coding region of v2.

Final amplicon 5 is obtained via assembly PCR of amplicons 3 and 4 for enabling the concatenation of the human VH and cynomolgus VH leader sequences.

1.3 Sequencing and Verification by the FDA (Food and Drug Administration) of the Final Vector The sequencing is effected through the method of Sanger (or method of the chain terminators, ref.: Sanger F. and al, 1977, PNAS 74: 5463).

Said technique involves the random incorporation of didesoxynucleotides (ddNTP), or "terminators", for generating, from a fixed end (fixing area of the sequencing primer), all fragments ending with a given base (A, C, G or T). Analyzing these fragments on an automatic sequencer (size-related separation and detection) enables to define the order of the various bases and therefore the sequence of a given DNA.

The sequencing procedures have been carried out according to the FDA quality grade. It is the highest quality level, with a double-stranded double coverage rate of sequenced DNA, a minimal redundancy of 4 times, a 100% accuracy, dedicated tools, quality report publishing and archival storage of the created documents.

After sequencing, the sequences provided by the supplier are compared in terms of alignment (software AlignX, Vector NTI, Invitrogen) with the theoretical expected sequence.

1.4 PCR Screening Primers
Primer 5prsvbis (SEQ ID N° 35)
5'-GCTCGATACAATAAACGCCA-3'

A primer located in the TU (transcription unit) intron K or H, used with CK4 or GSP2ANP, enables to detect VK inserts (781 pb amplicon) and VH inserts (821 amplicon) after cloning.

Primer CK4

(SEQ ID N° 36)
5'-TCTGGGATAGAAGTTATTCAG-3'

A primer located in 5' of the human constant region CK, used with 5prsvbis, enables to detect VK inserts after cloning.
Primer GSP2ANP (SEQ ID N° 37)
5'-GGAAGTAGTCCTTGACCAGGCAG-3'

A primer located in 5' of the human constant region G1, used with 5prsvbis, enables to detect VH inserts after cloning.

1.5 Intermediate Vector K558-12

1.5.1 Cloning in the Vector CHK463-23

This step performs the cynomolgus-human chimerization of the kappa chain of IgG 35PA$_{83}$ v2.

After amplification via assembly PCR and digestion through Spe I and Dra III, the sequence VKv2 was cloned in the vector CHK463-23 in the unique sites Spe I and Dra III to that end.

After ligation, the recombinant colonies have been screened to detect the presence of the insert by PCR using primers 5prsvbis and CK4 (781 pb amplicon).

From the 23 bacterial clones that were screened by PCR, 20 were recombinant, and did carry insert VKv2. After purification of the plasmids, clones 1 to 8 have been controlled through restriction Nde I (8536, 1246, 943 bases), Dra III (linearization) and Spe I (linearization).

1.5.2 Sequencing of Region VKv2 of the Intermediate Vector K558-12

The 8 identified recombinant clones have been controlled by sequencing with primer CK4.

Clones 2, 3, 4, 5 and 8 had a correct sequence between cloning sites Spe I and Dra III. However, clones 1 and 6 contain mutations and clone 7 could not deliver processable results.

Clone 55806231-2 was retained for continuing the construction of expression vector HK558-12.

1.6 Final Vector HK558-12

1.6.1 Cloning in Vector K558-12

This step performs the cynomolgus-human chimerization of the heavy chain of the antibody (IgG 35PA$_{83}$ v2).

After amplification via assembly PCR and digestion through Nhe I and Apa I, the sequence VHv2 was cloned in the intermediate vector K558-12 in the unique sites Nhe I and Apa I to that end. After ligation, the recombinant colonies have been screened to detect the presence of the insert by PCR using primers 5prsvbis and GSP2ANP (821 pb amplicon). From the 22 bacterial clones screened via PCR, 18 were recombinant, and did carry insert VHv2.

1.6.2 Sequencing of Region VHv2 of the Final Vector and Control through Restriction After purification of the plasmids, clones 1 to 5, 7, 9 and 11 were controlled by sequencing with primer GSP2ANP.

Clones 2, 4, 7 and 9 had a correct sequence between sites Nhe I and Spe I while the four other clones contained mutations.

Restriction controls were conducted on clones 2, 4, 7 and 9. The restriction assay Nhe I (linearization), Apa I (linearization) and Bgl II+Nde I (2900, 2222, 1975, 1879, 1246, 934, 9 pb) could confirm that the four clones had the expected restriction profile.

Clone 55806298-9 was selected for expressing the cynomolgus-human chimeric antibody (IgG 35PA$_{83}$). The map of this vector is illustrated on FIG. 4.

1.6.3 Control of the Final Vector via Digestion

A digestion Not I (linearization) and a double digestion Bgl II+NdeI (2900, 2222, 1975, 1880, 1246, 934, 9 pb) have been performed to control the purified plasmid derived from selected clone 55806298-9.

The resulting restriction profile corresponding to the one expected, clone 55806298-9 was sequenced according to FDA grade. The sequence was conform to what was expected.

1.6.4 Preparation of Vector HK558-12 for Transfection

The preparation of vector HK558-12, linearized by Not I (cf. paragraph 1.6.3), in TE buffer (10 mM Tris pH 8 and 1 mM EDTA) was stored at −20° C. before adjustment to the concentration of 1 µg/µl and transfer to the Cellular Engineering sector for transfection in YB2/0 and CHO cell lines.

Example 3

Preparation of Transformants that Produce the Cynomolgus-Human Chimeric Monoclonal Antibody 35PA83 v2 Directed Against the Protective Antigen of Anthrax 35PA83 v2 antibody was produced in YB2/0 cell lines (antibody EMABling®) and in CHO cell lines (antibody non EMABlinging®) in order to study the effect of glycosylation on its toxin-neutralizing activity in vitro and in vivo.

For the hereunder experiments, the implemented ELISA procedure is performed under following conditions:

Microtitration 96-well plates (maxisorp, Nunc, Danemark) were coated with PA diluted in PBS (5 µg/ml, 100 µl per well), overnight at 4° C. Plates were blocked by adding 200 µl of PBS-BSA 5% at 37° C. for 1 hour, and serially diluted serums in PBS-0.1% Tween 20-1% BSA were incubated (100 µl per well) at 37° C. for 2 hours. An anti-mouse IgG alkaline phosphatase conjugate or an "anti-human IgG alkaline phosphatase conjugate" (Sigma) were incubated ($1/10\,000$) at 37° C. for 1 hour. A P-Nitrophenyl Phosphate substrate was then incubated for 30 minutes at room temperature. The results were determined by measuring absorbance at 405 nm with an automated microplate reader. (iEMS reader MF, Labsystems, Helsinky, Finland). The last dilution which reversion determines the serum titer is determined as providing a signal lower than or equal to 2 times the naive serum used as a negative control.

The preparation scheme of transformants in YB2/0 cell line is illustrated in Table 4, at the end of the present specification.

1.1 Control of the Transformation Quality

Transformation Rate

The transformation rate was evaluated based upon the cell growth rate in P96 five weeks after culture at D+3 in a selective medium.

When performing a single selection with selecting agent G418, the transformation rate is of about $1/500$ to $1/900$. In case of a double selection with selecting agents G418 and MTX (methotrexate), it is higher than $1/2200$.

Average Production Rate 3 pools of 8 P24 wells were prepared when the wells were filled with cells up to ¾ to obtain a maximum production (D+7) for evaluating the average production.

These pools enable to evaluate the mean characteristics of a given population to make sure that a minimal characteristic level is attained, while the data concerning the transformants are not yet available.

The average production with vector HK558-12 and the vector control combination is respectively of 1.2 µg/ml and 3.3 µg/ml.

1.2 Cloide Selection

Production Rate: First Screening of the Most Productive Cloides

The production of human IgG was determined by ELISA on the supernatants of the double selection P96 wells containing ¾ of cells so as to obtain a first prioritization of the cloides as regards their production ability.

Three successive screenings (every 2 or 3 days) were carried out and the 10 best first producers for each screening have been retained. From 528 transformants, 27 were continued and preserved in P24 and a study was effected at the same time concerning their yield at D+3 and their maximum production (D+7).

Yield at D+3 and Maximum Production (D+7)

The 15 best first cloide producers selected with a yield for most of them higher than 5 pcd and a maximum production higher than 10 µg/ml have been amplified at the cellular level in a selective medium (double selection) for preservation in liquid nitrogen.

Fucose Rate

A fucosylation assay on the supernatants of the 15 selected cloides at D+3 and D+7 was effected by ELISA.

1.3 Selection of Cloide DD12 and Production of IqG in Roller

Cloide DD12 was retained for the production of IgG in rollers (19L) as it was the best cloide in terms of yield (11.6 pcd), maximum production (20.17 µg/ml) and fucose rate (26.9% at D+3 and 26.7% at D+7) selection criteria.

461 mg of antibody were produced for purification. After concentration (×15) and purification, 351 mg of antibody were obtained i.e. an amount that is sufficient for conducting the preliminary assays in vivo.

1.4 Cloning of 3 Cloides

The 3 best first producer cloides DD12, FH2 and GA11 (yield higher than 10 pcd, maximum production higher than 20 µg/ml and fucose rate lower than 33%) were cloned with limit dilution so as to preempt the possible instability of the transformants.

IgG Production: First Screening of the Best Producer Clones

The production of human IgG was determined by ELISA (Enzyme Linked Immunosorbent Assay) on the supernatants in the P96 wells containing ¾ of cells so as to obtain a first prioritization of the clones as regards their production ability.

Two successive screenings (7 days therebetween) were carried out and the 8 best producer clones of each cloide were retained. The yield is higher than 6 µg/ml.

Yield at D+3

Yield at D+3 for these 24 clones was calculated so as to select the 15 best producer clones, i.e. 5 clones/cloide. It is for most of them higher than 4 pcd.

The 15 selected clones have been amplified at the cellular level for preservation in liquid nitrogen.

1.5 Selection of Clone DD12-8F2

Clone DD12-8F2 was retained as the best one, based upon the yield (6.6 pcd) and fucose rate at D+3 (27.8%) selection criteria.

The characteristics of clone DD12-8F2 are close to those of its parental cloide DD12, except for yield (D+3) which was lower because of the various media used. Yield of the clones being homogeneous, it confirms the stability of the cloide.

1.6 Preparation of Transformants in the CHO Cell Line

The flow-chart corresponding to the preparation of the transformants that produced antibodies 35PA83 v2 in the CHO cell line is given in Table 5 at the end of the present specification.

2.1 Control of the Transformation Quality

Transformation Rate

The transformation rate was evaluated based upon the cell growth rate in P96 five weeks after culture at D+3 in a selective medium.

2.2 Cloide Selection

Production Rate: First Screening of the Most Productive Cloides

The production of human IgG was determined by ELISA on the supernatants in the P96 wells, in simple and double selection, containing ¾ of cells so as to obtain a first prioritization of the cloides as regards their production ability.

Three successive screenings (every 2 to 4 days) were carried out and the 10 best first producers for each screening have been retained. From 953 transformants, 30 were continued and preserved in P24 and a study was effected at the same time concerning their yield at D+4 and their maximum production (D+7).

Yield at D+4 and Maximum Production (D+7)

The 15 best first cloide producers selected with for most of them a yield higher than 1 pcd and a maximum production higher than 1 μg/ml have been amplified at the cellular level in a selective medium (simple or double selection depending on the preparation conditions) for preservation in liquid nitrogen.

Fucose Rate

A fucosylation assay on the supernatants of the 15 selected cloides at D+7 was effected by ELISA.

Fucose rate of the resulting IgG in the CHO cell line is typically higher than 75%.

2.3 Gene Amplification

For transformants with low production rates and unable to produce the antibody required amounts, a gene amplification was carried out to increase the copy number of integrated vectors and therefore the yield of the amplified cloides.

Gene amplification was performed on 3 cloides (13G8, 9D4 and 8F11) and 2 cloide groups (1 pool of 4 cloides (PA1) and 1 pool of 8 cloides (PA2)). This choice was made while taking into account the globally results obtained for yield at D+4, maximum production and fucose rate.

Gene amplification was performed by transplanting the cells into a selective culture medium with G418 and MTX. The amplification first step was performed with a MTX concentration of 5 nM for the cloides prepared without MTX and of 40 nM for the cloides prepared with 10 nM MTX. The IgG production at D+4 was then carried out.

Further amplification steps followed, while increasing the MTX concentration ×4 in the amplification second step and ×16 in the amplification third step.

Analyzing the production rates at D+4 reveals an increase in the production of IgG during the amplification process. Indeed, the yield is approx. four times as high as that obtained before gene amplification.

2.4 Selection of Two Cloides and Production in Roller of Cloide 13G8

Cloides 13G8 and 9D4 have the best production rate after amplification with a maximum yield reached in the amplification second step.

Cloides 13G8 (20 nM MTX) and 9D4 (160 nM MTX) have thus been amplified at the cellular level in a selective medium for preservation in liquid nitrogen.

Following the fucose rate assay performed on the purified IgGs derived from both cloides 13G8 and 9D4, cloide 13G8 (20nM MTX) was retained for the production of IgG in rollers (5.5 L). The fucose rate relative to purified IgGs was of 76.6%.

65.5 mg of IgG were produced for purification. After purification, 46.2 mg of antibody were obtained.

2.5 Conclusion

As regards the production in YB2/0 cell line, cloide DD12 was retained as the best one, considering all the selection criteria, with a yield of 11.6 pcd, a maximum production of 20.17 μg/ml and a fucose rate of about 27%.

The production in roller (19 L) of this cloide enabled to obtain 351 mg of purified antibodies with a fucose rate of 26%.

For the production in the CHO cell line, cloide 13G8 (20 nM MTX) was retained as the best one, considering all the selection criteria, with a yield of 8.2 pcd and a fucose rate relative to purified IgGs of 76.6%.

The production in roller (5.5 L) of this cloide enabled to obtain 46.2 mg of purified antibodies with a fucose rate of 84%.

The amounts of purified antibodies resulting from both cell lines were therefore sufficient for enabling conducting the first in vivo assays.

Example 4

In Vitro Neutralization Assays

After the production of DD12 in YB2/0 cells, the supernatant in the cell culture was recovered, concentrated ×15, then submitted to an affinity chromatography using a A-Sepharose recombinant protein. A second purification step was performed by means of a cation exchange column HiPrep 16/10 SP FF. The purified IgG integrity and the absence of any contaminant were controlled via SDS-PAGE and via ELISA for the binding to recombinant PA83.

Affinities were measured by surface plasmon resonance (SPR) using the BIAcore™ (Biacore Uppsala, Sweden). PA83 (List biological laboratories, Campbell, Calif.) was immobilized at 210 RU maximum onto a CM5 chip (Biacore) through an amine bond, in accordance with the supplier instructions. A 30 μl/min flow was maintained during the measurement procedure. For each measurement, at least 6 dilutions of IgG in HBS-EP buffer (Bioacore), with concentrations ranging from 10 to 0.1 μg/ml, were tested for 1900 seconds. After each dilution of IgG, the chip was regenerated with glycine pH 1.5 (Biacore), with a 10 μl/min flow for 30 seconds. The constants were calculated through a method of bivalent analyte (Karlsson and al. 1991), and checked through internal consistency tests (Schuck and al. 1996).

The in vitro neutralization test was carried out according to the protocol described by Little and al. (Little and al., 1990). The mouse macrophage cell line J774A.1 (ATCC-LGC, Molsheim, France) was incubated for 16 h at a concentration of 14000 cells/well on a 96-well plate. The components of lethal toxin, 400 ng/ml of PA (List laboratories) and 40 ng/ml of LF, each being diluted in PBS at 1 mg/ml and stored in a frozen state until use, were simultaneously added to IgG or to the medium alone and incubated for 1 hour at 37° C. The incubation product was then added to the macrophages and incubated at 37° C. for 4 hours. The Cytotox® assay (Promega) was used in accordance with the supplier instructions for evaluating the viability of the cells. Each assay was corrected to a cell viability of 100% (the control wells were those which did contain neither toxin nor IgG) and to a viability of 0% (the control wells being those which did contain the toxin but not IgG).

Results: The apparent affinity of IgG 35PA83 measured was of 80 pM and the 50% neutralization value ($IC_{50}$) measured was of 0.75±0.02 nM (average±SD), which represented: (IgG 35PA83/PA) of ¼ or a ratio (IgG 35PA83 binding sites/PA) of ½.

Example 5

Pharmacokinetic Analysis

For evaluating half-life of IgG 35PA83, six A/J mice of six weeks of age (Harlan, Gannat, France) were distributed into two subgroups of the same size. All the mice received IgG 35PA83, administered by a single subcutaneous injection at a dose of 10 mg/kg. Blood was collected by a daily retroorbital puncture, from day 1 and until day 6 post injection, then from day 8 until day 10 post injection, by using each distinct day mice alternately. Half-life of IgG 35PA83 was determined from the results of the ELISA tests performed on serum sample pools, after linear extrapolation of the obtained values.

For performing the ELISA tests, the wells of the microtitration 96-well plates were covered by incubation with antigen PA83 or antigen LF (List Laboratories) diluted in a PBS buffer (5 µg/ml, 100 µl per well) for one night at 4° C. The free sites in the microplate wells were then blocked by incubation with a volume of 200 µl of a 5% solution of bovine serum albumin (BSA) in a PBS buffer, for 1 hour at 37° C. The dilution of the serums were made in series in a buffer of PBS 0.1%, Tween®20, BSA 1%, then incubated within the plates (100 µl/well), for 2 hours at 37° C. The plate wells have been then incubated with an anti-mouse IgG/alkaline phosphatase conjugate or an anti-human IgG/alkaline phosphatase conjugate diluted at 1/10 000 (Sigma, Saint Louis, Mo., United States), for 1 hour at 37° C. The P-nitrophenyl phosphate substrate (Sigma) was then added thereto and the plates have been incubated for 30 minutes at the laboratory temperature. The absorbance was determined at 405 nm by using an automatic microplate reader (iEMS reader MF, Labsystems, Helsinki, Finland). The limit dilution point was defined, which reciprocal value corresponds to the serum antibody titer, as being the point where the signal value was twice as high as that of the measured signal for the naive mouse serum. The naive mouse serum was used as a negative control.

Results: Half-life of IgG 35PA83 in A/J mice was determined as being of 7.78±1.46 day.

Example 6

Passive Protection Assays in Rats

For in vivo assays were injected to Fischer rats (weighting 250 to 300 g) (C. River, L'Abresle, France) 40 µg of PA (List biological laboratories, Campbell, Calif.) and 8 µg of LF per 250 g of rat, as described in Ezzel and al. (Ezzell and al., 1984), except that the vein of the tail was used. 4 animals per group were used and for evaluating IgG 35PA83, IgG was added to PA and to LF prior to the injection. Rats were observed twice a day for 10 days. All the in vivo assays presented in this study were approved by the local animal experiment and care ethics committee.

Preparation and Use of Sterne Strain Spores:

B. anthracis Sterne strain spores (collection Pasteur) were prepared as stated in Albrecht and al. (Albrecht and al., 2007), and were stored under frozen conditions (−20° C.). The spores were counted by counting the viable plates after freezing/thawing and the count was verified when each tube was used in this study. The LD50 values of these spores administered intravenously to A/J male mice (Harlan, Gannat, France), of 9 weeks of age and weighting 20 to 25 g, were determined at $1.10^4$, causing death within 48 to 72 hours, close to the $2.10^4$ value used in another study (Albrecht and al., 2007).

Results: rats injected with toxins died within only 2 hours. When protected with 0.15 nmol of IgG 35PA83, only 2 rats died at 4.5 hours and 5 hours (effect statistically considered as significant, p=0.045). The 4 rats did survive when 0.2 nmol of IgG 35PA83 was used (significant effect, p=0.03), corresponding to a molar ratio (binding sites to antigen of IgG/PA83) of 0.8.

Example 7

Prophylactic Treatment with IgG 35PA83 v2, Short Treatment with Tetracycline, or Both For the study of a prophylactic treatment with IgG 35PA83 v2 or with tetracycline only, IgGs were injected to groups of 10 A/J mice, by subcutaneous route, 12 hours prior infection (one injection of 5 mg/kg or of 2 mg/kg). The challenge was administered as 10 000 LD50 or $1.10^8$ spores and mice were observed twice a day for 2 weeks, then 5 times a week for 2 additional weeks. The surviving mice were tested again by being infected one month later with the same amount of spores, and observed for one additional month. For the study of a prophylactic treatment involving both tetracycline and IgG 35PA83, 10-mice groups were treated with tetracycline in the same way as in the program using tetracycline alone except that IgG 35PA83v2 was injected in addition 12 hours before challenge. For testing the active protection, 10 mice were injected by subcutaneous route with 5 μg of PA per mouse, in Freund's complete adjuvant. A second group received the same injection then, 1 month later, the immune response of this group was stimulated with the same dose of PA in Freund's incomplete adjuvant.

Results: The prophylactic treatments started 12 hours before a challenge of 10 000 LD50 and survival curves are illustrated on FIGS. 5 and 6 (tetracycline, 7 days). All the mice having been administered 5 mg/kg of IgG 35PA83 did survive and 60% of the mice having been administered 2 mg/kg of IgG 35PA83 did survive (significant, p<0.0001). From these 16 surviving mice, one month following the injection of the 35PA83 and challenge, it could not be detected any antibody by means of the human anti-IgG conjugate, and it was therefore considered that no IgG 35PA83 was yet contained at this stage. Mice titers in murine IgG directed against PA were in the range from 64 000 to 128 000, and their titers in murine IgG directed against LF were in the range from 32 000 to 64 000, independently from the received dose. When these mice were challenged again with 10 000 LD50 of Sterne strain spores, one month after the initial infection, all did survive.

All the mice having been administered a prophylactic treatment with tetracycline did survive during the treatment (7 days). However, these mice died within 4 to 7 days following the discontinuation of antibiotics administration. When this last injection had been complemented with one injection of IgG 35PA83 at a dose of 1 mg/kg, 20% of the mice did survive (non-significant result) but all of them did survive when a dose of 2 mg/kg was used (significant, p=0.008). Mice which were actively protected by one injection of PA had an anti-PA antibody titer ranging from 25 000 to 50 000 one month later. Thereafter they were challenged, and from the 10 mice 6 did survive (considered as significant, p=0.01). Mice which were actively protected by 2 injections of PA had an anti-PA antibody titer ranging from 160 000 to 640 000 1 month after the second injection, and all did survive.

Thus, the tests performed revealed that one injection of IgG 35PA83 v2 enabled to shorten the tetracycline-based prophylaxis and, when the antibody has been injected one time at a dose of 2 mg/kg at the end of the prophylactic treatment, a 100% survival could be observed in mice. By contrast, mice protected through a short treatment with tetracycline (7 days) were injected with 1000 LD50 of *B. anthracis* Sterne strain, 12 hours after having started the treatment, 60% of the mice did survive. After a challenge with 10 000 LD50, all the mice having been administered the tetracycline died less than 7 days following the discontinuation of antibiotics administration, probably due to a late spore germination. Thus, this demonstrates that a prophylactic treatment with tetracycline may be stopped, in a secured manner, after an exposure risk, through a short treatment with tetracycline followed with an injection of IgG 35PA83. This solution makes it advantageously possible to envisage the antibiotics intake by patients, since such medication period is shorter, and to foresee a cost reduction due to the antibiotics dose lowering.

Example 8

Prophylactic Treatment with IgG 35PA83 v2, Short Treatment with Doxycycline, or Both The study of a prophylactic treatment with doxycycline, with or without IgG 35PA83, was effected on 10-A/J mice groups aged of 10 weeks (Harlan, Gannat, France), to which the antibiotic was injected as a prophylaxis via the intraperitoneal route, at a single daily dose of 5 mg/kg. Chemoprophylaxis started 12 hours prior infection and was continued for 7 days, which represents a 9/10 reduction of the standard duration which is of 60 days.

A doxycycline dosage was chosen, which was approximately twice as high as the human standard dosage (daily dosage of 3 mg/kg for a human adult), and it could be demonstrated that smaller doses were efficient against *B. anthracis* (Friedlander and al., 1993, J Infect Dis, Vol. 167: 1239-1243; Kalns and al., 2002, Biochem Biophys Res Commun, Vol. 297: 506-509). Higher doses have been used (Heine and al., 2007, Antimicrob Agents Chemother, Vol. 51: 1373-1379); however it could be observed that a dose of 50 mg/kg seemed to be not well tolerated in A/J mice, which suffered from an abdominal swelling and a piloerection. For complementing the treatment with doxycycline with IgG 35PA83, a single dose of this antibody (1 or 2 mg/kg) was injected or not concomitantly to the last doxycycline dose. The infection used $1 \times 10^8$ injected spores via the intraperitoneal route, which represented 10 000 $LD_{50}$. Mice have been observed twice a day for the first two weeks, then five times a week for the two additional weeks.

Results: After anthrax dissemination in the United States in 2001, it had been noted an incomplete observance of the long-lasting prophylactic treatment (60 days) with antibiotics. To determine whether IgG 35PA83 could reduce the treatment duration, a prophylactic treatment was initiated, with a daily dose of 5 mg/kg of doxycycline for only 7 days, 12 hours prior infection with 10 000 $LD_{50}$. On the last day of the treatment, the prophylactic treatment with antibiotics was complemented, or not, with a single injection of IgG 35PA83 (FIG. 7). However, when this last injection of doxycycline was complemented with 1 mg/kg of IgG 35PA83, the average duration until death was increased to 288-456 hours and 20% of the mice did survive, which represents a significant protecting effect (comparison versus doxycycline, p<0.001). At a dose of 2 mg/kg of IgG 35PA83, the all ten animals did survive. One month post infection, serums of the twelve surviving mice have been systematically collected, combined in pools, and stored at −20° C. Once the serums had been tested via ELISA, the anti-PA IgG antibody titer was on average of 64 000 and the anti-LF IgG antibody titer was on average of 32000.

Example 9

Therapy with IgG 35PA83 v2, Ciprofloxacin Short Treatment or Both

For studying the therapeutic scheme, A/J mice groups of 10 individuals were challenged with a dose of 1000 LD50 or $1.10^7$ spores. After 12 hours, IgG 35PA83 v2 (subcutaneous, 1 injection of 10 mg/kg) or ciprofloxacin (subcutaneous, 50 mg/kg twice a day for 5 days) were injected separately or ciprofloxacin and IgG 35PA83 were both injected on the first day, then ciprofloxacin alone was further injected for 4 additional days.

Figure 8:
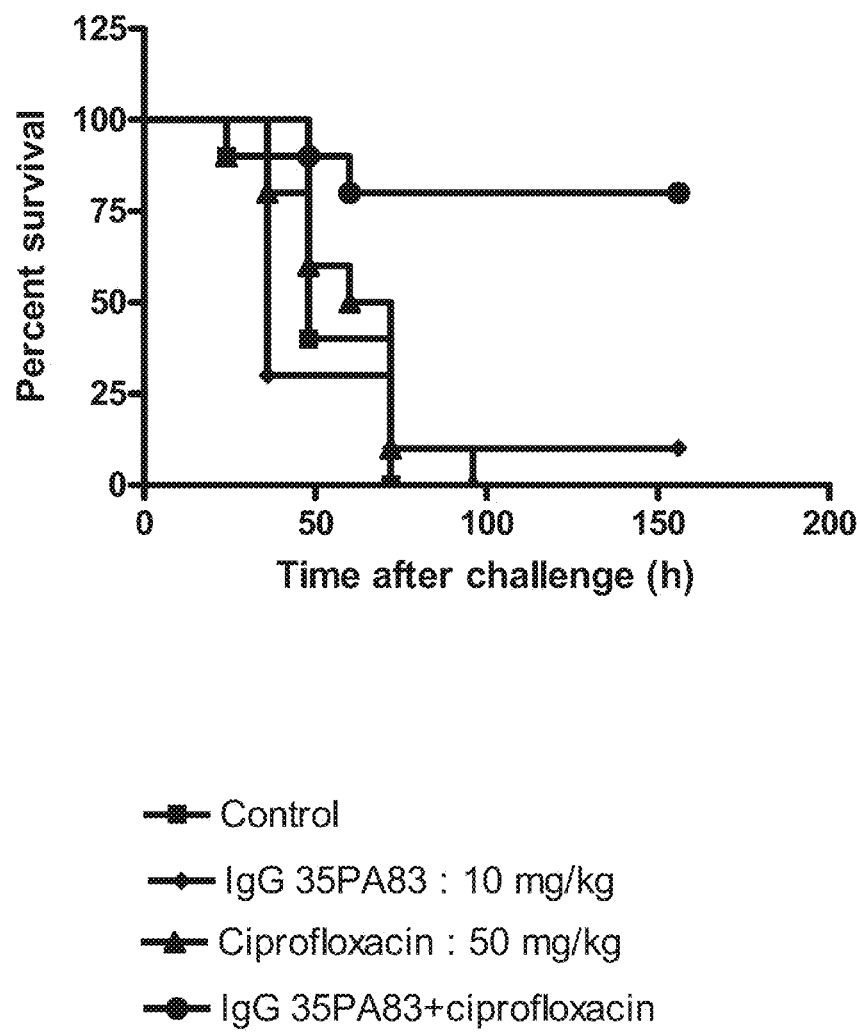
FIG. 8: ciprofloxacin-based treatment, IgG 35PA83 v2 or both. Ciprofloxacin or IgG 35PA83 v2 used alone enables substantially no survival, whereas a combination of both molecules enables a survival rate of 80%. No new event could be observed until day 30.

Results: The therapeutic treatments started 12 hours after a challenge of 1000 LD50 and survival curves (ciprofloxacin, 5 days of treatment or IgG 35PA83 or both) are illustrated on FIG. 8. None of the mice having been administered ciprofloxacin for 5 days did survive, only 10% of the mice having been administered IgG 35PA83 did survive (non-significant result). However, 80% of the mice having been administered both ciprofloxacin and IgG 35PA83 did survive (significant, p=0.0007).

Simultaneously using ciprofloxacin and IgG 35PA83 enabled to obtain a survival of 80%. A strong synergism of IgG PA83 and ciprofloxacin was demonstrated in therapeutic use, and, interestingly, no vaccine enables such a short antibiotic treatment (5 days), since such a time limit does not allow to generate an immune response. In addition, IgG 35PA83 most probably prevents relapses after this short antibiotic treatment, and for this reason, it could even be more efficient for humans for whom its half-life is expected to be at least 3 times longer than in mice (from 3 to 7 days vs. 21 days).

Example 10

Therapy with IgG 35PA83 v2, Ciprofloxacin Short Treatment or Both (Other Assay)

For the studies of curative treatment, A/J mice groups of 10 individuals were infected with a dose of 1000 $LD_{50}$ or $1.10^7$ spores. After 12 hours, mice have been treated with ciprofloxacin (subcutaneous, with one initial injection of 25 mg/kg) or with IgG 35PA83 v2 (subcutaneous, 1 injection of 10 mg/kg) separately; or ciprofloxacin and IgG 35PA83 were both injected simultaneously in two different sites. Additional delays were also tested, of 24 hours and 48 hours prior to starting the combined treatment (ciprofloxacin and IgG 35PA83). After the first administration of the treatment, ciprofloxacin alone (25 mg/kg, twice a day) was injected during the 4.5 following days. The dose of ciprofloxacin was chosen as being approximately twice as high as the human standard dose (daily dose of 20 mg/kg in human adult), this dose having already been efficiently used against *B. anthracis* (Kalns and al., 2002, Biochem Biophys Res Commun, Vol. 297: 506-509). The tolerance to this selected dose was favorably tested in A/J mice prior to starting this study. This part of the study substantially aims at solving the problem of the short-term survival after a delayed treatment, and the monitoring was limited to the 18 day-post infection period.

Figure 9:
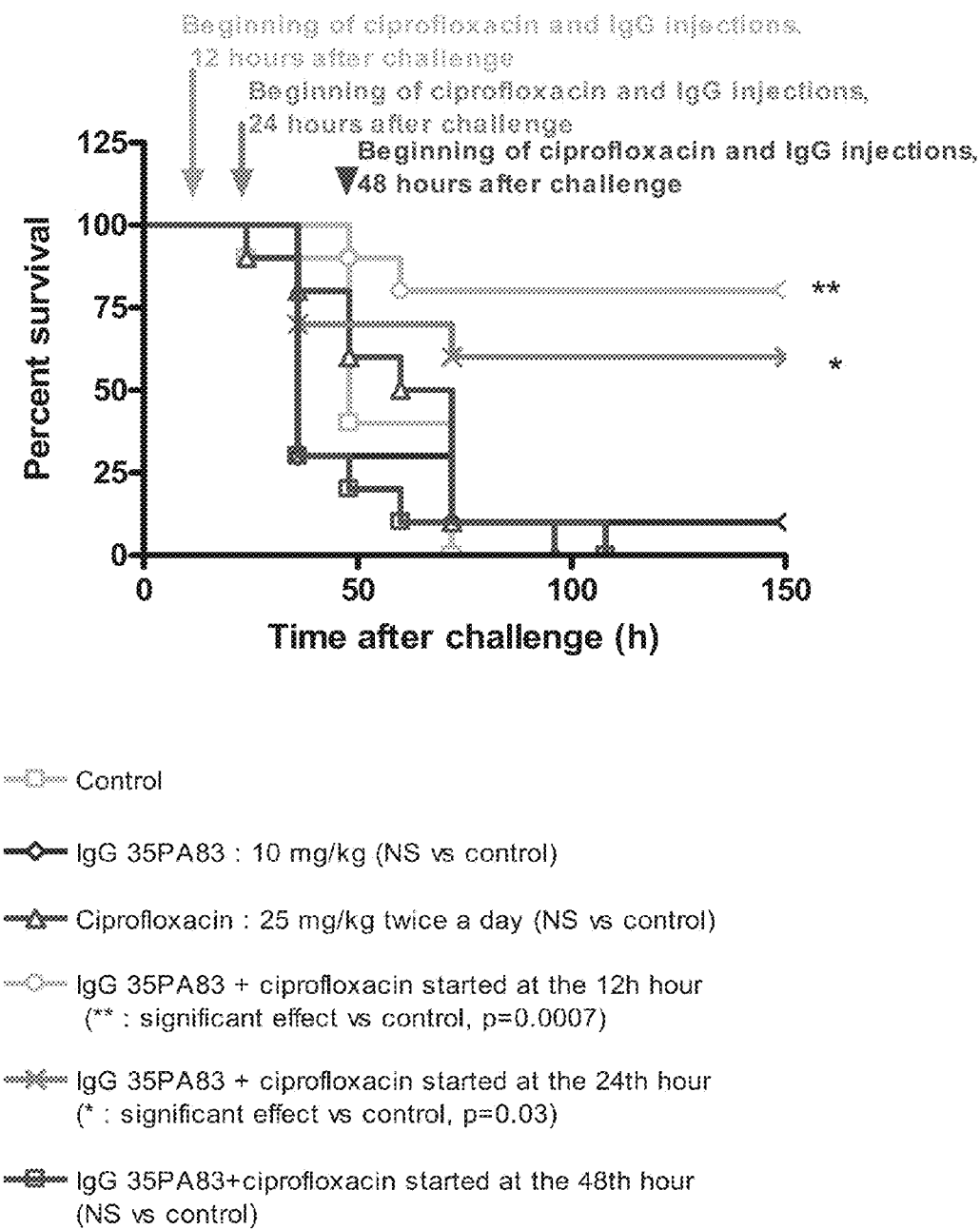
FIG. 9: Treatment with ciprofloxacin, complemented or not with IgG 35PA83. A/J mice were infected with 1000 $LD_{50}$ Sterne spores. Twelve hours post infection, in two separate groups (10 animals in each group), a ciprofloxacin-based treatment alone was initiated (25 mg/kg twice a day) for five days, or a single dose of IgG 35PA83 (10 mg/kg) was injected. At three different times post infection (12, 24 or 48 hours), each time being represented by a different group of animals, mice received a combined ciprofloxacin-based treatment (25 mg/kg twice a day for five days) plus one injection of IgG 35PA83 (10 mg/kg). No special event could be observed beyond the time period illustrated on the figure ($150^{th}$ hour). The significant effects are indicated on the figure with sign "*" ($p=0.03$) or "**" ($p=0.0007$).

Results: anthrax is seldom encountered in the current praxis and its diagnosis as well as its treatment most likely will be delayed. In this study, single treatments (five-day long ciprofloxacin treatment at a dose of 50 mg/kg/day or a single dose of 10 mg/kg of IgG 35PA83) have been delayed for 12 hours after an infection with 1000 $LD_{50}$ of Sterne strain spores, and the combined treatments (ciprofloxacin combined with IgG 35PA83) have been delayed for 12, 24 and 48 hours after the same infection (FIG. 9) and tested for their efficiency. Mice treated with ciprofloxacin alone did not survive and the treatment with IgG 35PA83 alone enabled to obtain the survival of only one mouse from the all ten of the assay (non-significant result). However, 80% of the mice treated with both ciprofloxacin and IgG 35PA83 did survive when the treatment was delayed for 12 hours (significant as compared to the non treated control, p=0.0007), and 60% of the mice did survive when the treatment was delayed for 24 hours (significant as compared to the non treated control, p=0.003). On the $48^{th}$ hour post infection with no treatment, only two from the ten mice had survived, but died shortly after, despite the combined treatment administered. Eighteen days post infection, serums of the fourteen surviving mice have been collected, combined in pools, stored, then tested via ELISA. The anti-PA IgG antibody titer was of 32000 and the anti-LF IgG antibody titer was of 8000.

Example 11

Comparison Between Passive and Active Prophylactic Anti-Anthrax Treatments

A passive prophylactic anti-anthrax treatment consists in a treatment with IgG 35PA83. An active prophylactic anti-anthrax treatment consists in a treatment through immunization with antigen PA.

For comparing the active and the passive immuno-protection, a ten-mice group was immunized by a subcutaneous injection of 5 µg of PA83 in Freund's complete adjuvant and infected intraperitoneally with 10 000 $LD_{50}$, one month later. Another ten-mice group was immunized in the same way, but received an "immunization recall" four weeks later with 5 µg of PA83 in Freund's incomplete adjuvant and, and thereafter was infected one month later with a second injection. At the same time, the passive protection with IgG 35PA83 against the same infection was evaluated. All the infected animals have been observed for one month, and the results of both prophylaxis types have been compared.

Figure 10:
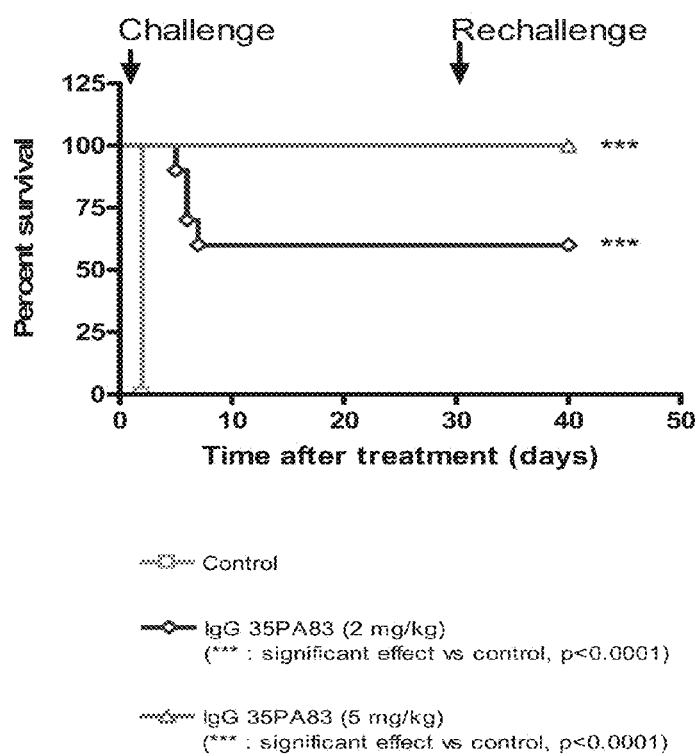
FIG. 10: Passive prophylactic treatment with IgG 35PA83. One injection of 35PA83 (2 mg/kg or 5 mg/kg) was administered twelve hours prior infection (10 000 $LD_{50}$). Mice surviving beyond day 30 were reinfected (10 000 $LD_{50}$) on day 30. No special event could be observed beyond the time period illustrated on the figure ($40^{th}$ day). Highly significant effects are indicated on the figure with sign "***" ($p=0.0001$).
Figure 11:
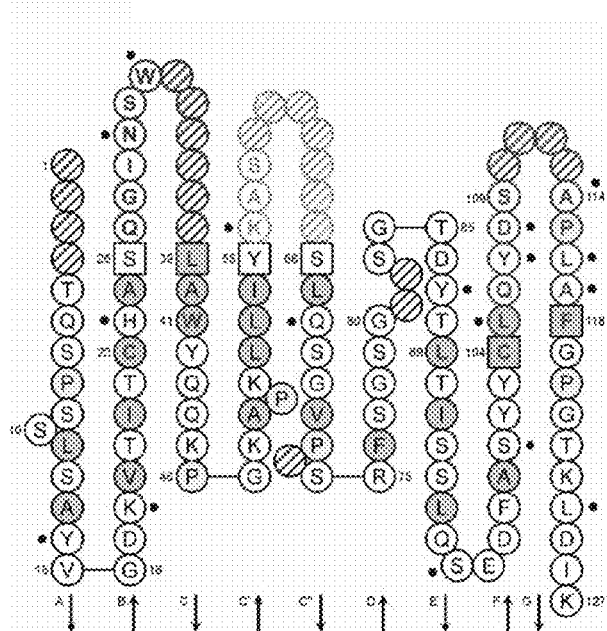
FIG. 11: pearl-on-a-string configuration of the heavy-chain variable region and of the light-chain variable region of non mutated 35PA83 antibody.
Figure 11:
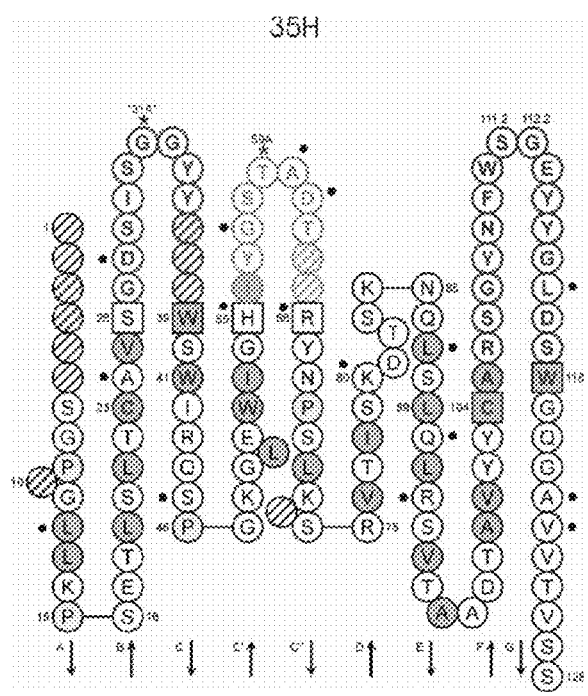

Results: the vaccination based on PA injection is traditionally the most often used prophylactic means against anthrax, and its efficiency is correlated with anti-anthrax antibody titers (Grunow and al., 2007, Vaccine, Vol. 25: 3679-3683). A/J mice were immunized with PA, so as to produce anti-PA titers with values similar to those observed in vaccinated humans, in order to compare the efficiency of such a vaccination with the protection provided with IgG 35PA83. Mice immunized with a single injection of PA83 had anti-PA antibody titers of from 25 000 to 50 000, one month after immunization. Mice have been infected with 10 000 $LD_{50}$ of Sterne strain spores, and six from the ten mice did survive (significant result of comparison with control naive mice, p=0.01). Ten mice immunized with two injections of PA83 had anti-PA83 antibody titers of 160 000 and 640 000 and these ten animals did survive to a similar infection, one month after the end of the immunization treatment, which demonstrates an increased level of significant protection (p=0.02) with a two injection-based treatment, as compared to a single injection-based treatment. At the same time, the passive protection with IgG 35PA83 has been evaluated, at doses of 2 or 5 mg/kg. Six from the ten mice protected with 2 mg/kg of IgG 35PA83 did survive (significant protection as compared to non treated mice, p<0.0001, FIG. 10), and all the mice having been administered prophylactic injections of 5 mg/kg of IgG 35PA83 did survive. In this study, the complete protection which was obtained through injection of 5 mg/kg of IgG 35PA83 was therefore equivalent to the complete protection obtained through two immunizations with PA83, which itself was higher than the protection provided through a single injection of PA83.

Mice having survived after the passive prophylactic treatment with IgG 35PA83 alone have been in addition observed for one month after the initial infection. In an ELISA test using PA83 as an antigen and anti-human IgG conjugate, no signal could be detected in the corresponding serums, and it was concluded therefore that there was no IgG 35PA83 in mice one month post injection, which coincides with the half-life value of IgG 35PA83. However, with the anti-mouse IgG conjugate, murine IgGs were detected, which were directed against PA with a titer ranging from 64 000 to 128 000, and murine IgGs directed against LF with a titer ranging from 32 000 to 64 000, independently from the dose of IgG 35PA83 administered. All the animals did survive to a re-infection with 10 000 $LD_{50}$ of Sterne strain spores, one month after the initial infection.

Table 7 hereunder summarizes the results of the anti-PA IgG antibody titers and anti-LF IgG antibody titers observed, under the four experimental conditions.

TABLE 7

| Experimental conditions | Anti-PA IgG antibody titer | Anti-LF IgG antibody titer |
|---|---|---|
| Prophylactic treatments with doxycycline and IgG 35PA83 (2 mg/kg): pool of 10 serums, collected one month post infection | 64 000 | 32 000 |
| Curative treatment with ciprofloxacin and IgG 35PA83: pool of 14 serums, collected 18 days post infection | 64 000 to 12 000 | 32 000 to 64 000 |
| Immunization with PA83: one injection, serums collected one month post injection | 25 000 to 50 000 | NR* |
| Immunization with PA83: two injections, serums collected one month after the second injection (recall injection) | 160 000 to 640 000 | NR |

*NP = Non Relevant

In Vivo Assay Statistics:

A Kaplan-Meier comparative log-rank test for analyzing the survival data was performed using a Graph Prism 4.0 software (GraphPad software, San Diego, Calif.).

Reference Works

Albrecht, M. T., H. Li, E. D. Williamson, C. S. Lebutt, H. C. Flick-Smith, C. P. Quinn, H. Westra, D. Galloway, A. Matezun, S. Goldman, H. Groen, and L. W. Baillie. 2007. Human monoclonal antibodies against anthrax lethal factor and protective antigen act independently to protect against *Bacillus anthracis* infection and enhance endogenous immunity to anthrax. Infect Immun.

Andris-Widhopf, J., C. Rader, P. Steinberger, R. Fuller, and C. F. Barbas, 3rd. 2000. Methods for the generation of chicken monoclonal antibody fragments by phage display. J Immunol Methods 242:159-181.

Andris-Widhopf, J., P. Steinberger, R. Fuller, C. Rader, and C. F. Barbas, 3rd. 2001. Generation of antibody libraries: PCR amplification and assembly of light—and heavy-chain coding sequences. In C. F. Barbas, 3rd, D. R. Burton, J. K. Scott, and G. J. Silverman (ed.), Phage Display: A Laboratory Manual. Cold Spring Harbor Laboratory Press, New York.

Carter, P., H. Bedouelle, and G. Winter. 1985. Improved oligonucleotide site-directed mutagenesis using M13 vectors. A nucleic acids Res 13:4431-43.

Ezzell, J. W., B. E. Ivins, and S. H. Leppla. 1984. Immunoelectrophoretic analysis, toxicity, and kinetics of in vitro production of the protective antigen and lethal factor components of Bacillus anthracis toxin. Infect Immun 45:761-7.

Karlsson, R., A. Michaelsson, and L. Mattsson. 1991. Kinetic analysis of monoclonal antibody-antigen interactions with a new biosensor based analytical system. J Immunol Methods 145:229-40).

Laffly, "Selection of a macaque Fab with framework regions like those in humans, high affinity, and ability to neutralize the protective antigen (PA) of *bacillus anthracis* by binding to segment of PA between residues 686 and 694", Antimicrobial agents and chemotherapy, August 2005, p. 3414-3420.

Little, S. F., S. H. Leppla, and A. M. Friedlander. 1990. Production and characterization of monoclonal antibodies against the lethal factor component of *Bacillus anthracis* lethal toxin. Infect Immun 58:1606-13.

Schuck, P., and A. P. Minton. 1996. Analysis of mass transport-limited binding kinetics in evanescent wave biosensors. Anal Biochem 240:262-72.

TABLE 4

Preparation of transformants in YB2/0 cell line

| STEPS | CONTROLS |
|---|---|
| 1 cryotube YB2/0 ATCC | |
| ↓ | |
| Thawing | |
| ↓ | |
| Culture medium EMS + 5% FCS | |
| ↓ | |
| Cell expansion by dilution at $1.10^5$ cell/ml, twice a week | Cell count<br>Cell viability<br>Time |
| ↓ | |
| Electroporation Transformation (D0) | |
| Electrobuffer + HK558-12 vector ↓ | |
| Dilution Distribution in P96? | |
| Culture medium* ↓ | |
| Selection (D + 3) of the Transformants | Cell count at D + 3 in a non selective medium<br>Transformation rate<br>3 Microscopic examination<br>Total number of well grown after 1 week |
| Selective culture medium* + G418 (0.5 g/L) ± MEX 25 nM ↓ | 8-well pools:<br>Cell count<br>Cell viability<br><br>Maximum production (D + 7)<br>IgG production in P96 |
| Selection of the first 27 best producer cloides by RD Biotech | Cell count (D + 3)<br>Cell viability (D + 3)<br>Yield (D + 3)<br>IgG maximum production (D + 7) |
| Selective culture medium* + G418 (0.5 g/L) ± MTX 25 nM ↓ | |
| Selection of 15 cloides by LFB | Fucose/production (D + 3)<br>Fucose/maximum production (D + 7) |
| *RPMI + 5% dialyzed FCS ↓ | |

TABLE 4-continued
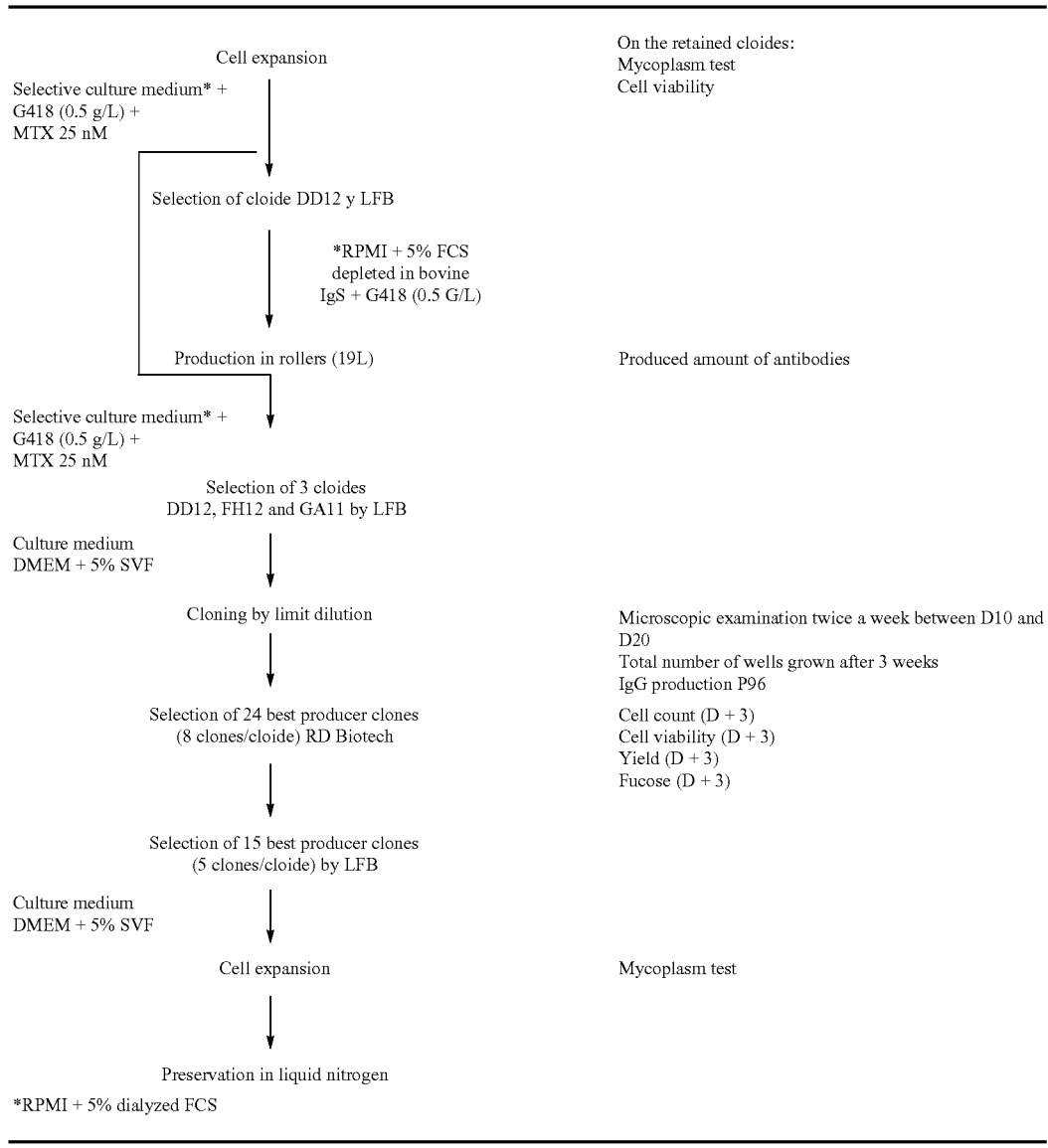

TABLE 5
Preparation of transformants in CHO cell line
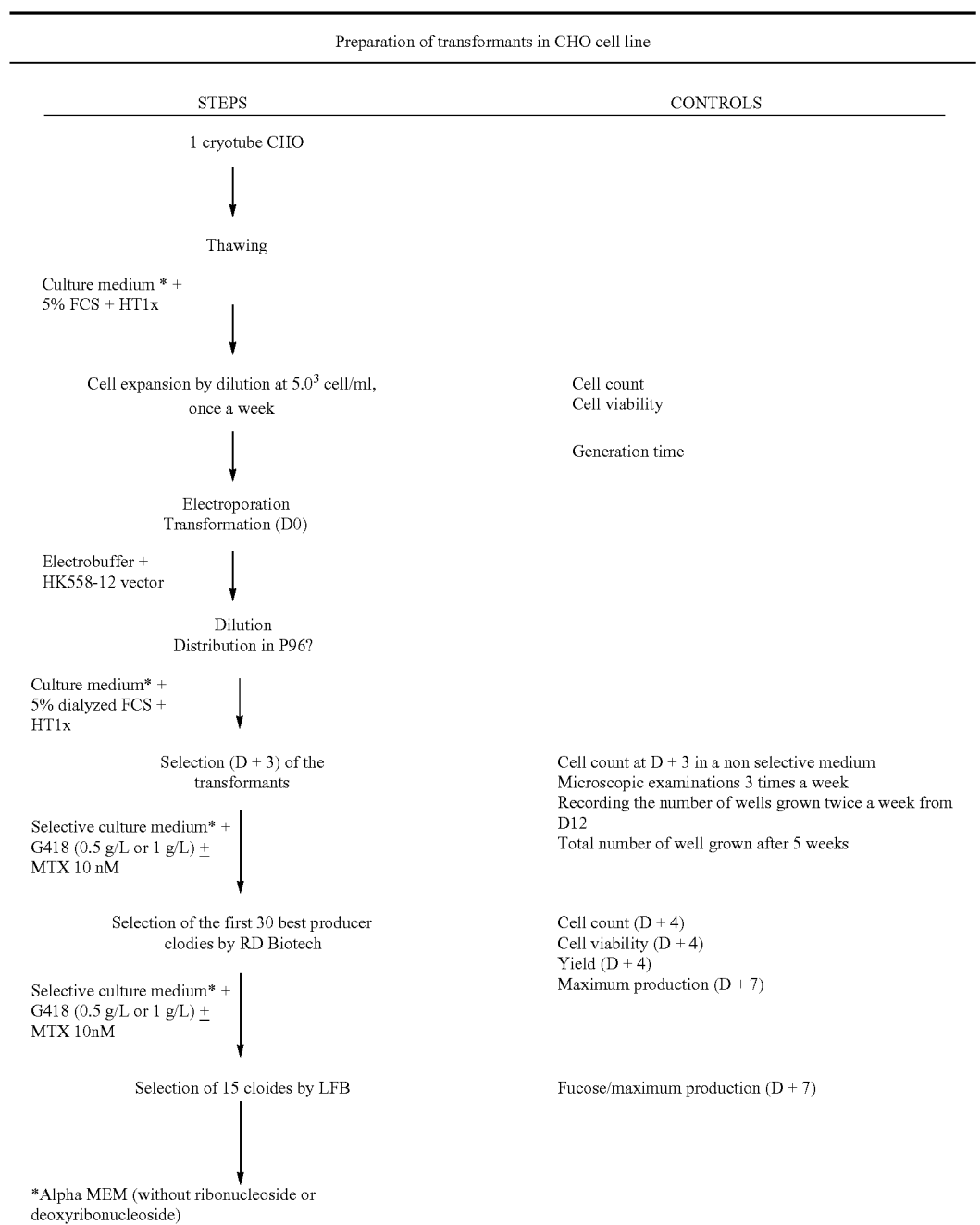

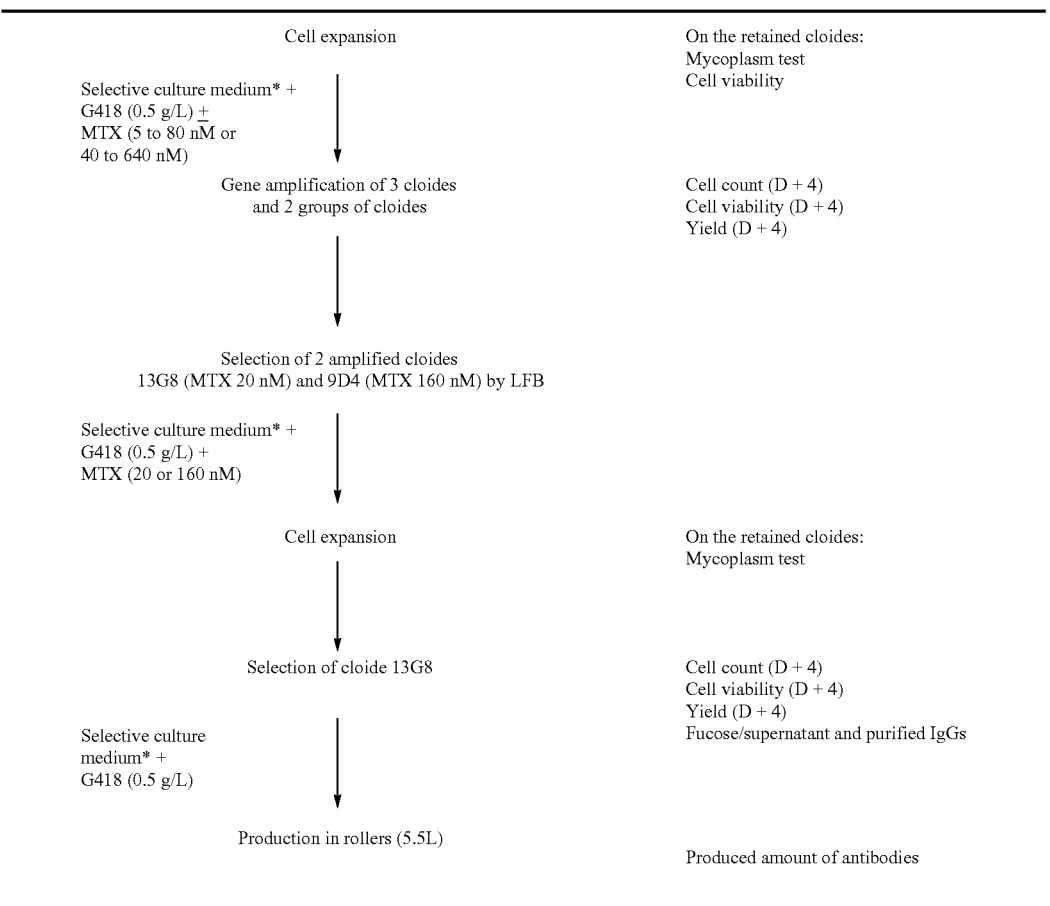

| TABLE 6 | | |
|---|---|---|
| Sequence listing | | |
| Sequence | Region | Type |
| 1 | light-chain variable region | peptide |
| 2 | heavy-chain variable region MUTE AFFINITE (31A, 66, 73) | peptide |
| 3 | light-chain constant region | peptide |
| 4 | heavy-chain constant region | peptide |
| 5 | IgG light chains | peptide |
| 6 | IgG heavy chains MUTE AFFINITE (31A, 66, 73) | peptide |
| 7 | variable region of each of the IgG light chains | Nucleic acid |
| 8 | variable region of each of the heavy chains MUTE AFFINITE (31A, 66, 73) | Nucleic acid |
| 9 | constant region of each of the IgG heavy chains | Nucleic acid |
| 10 | constant region of each of the light chains thereof | Nucleic acid |
| 11 | light chains of the antibody | Nuleic acid |
| 12 | heavy chains MUTE AFFINITE (31A, 66, 73) | Nucleic acid |
| 13-37 | primers | Nucleic acid |

The invention claimed is:

1. An IgG directed against a protective antigen (PA) of an anthrax toxin, wherein:
   a) the light-chain variable region has
      a1) the amino-acid sequence of SEQ ID NO: 1, or
      a2) the amino-acid sequence of SEQ ID NO: 1 and further comprising at least one mutation selected from the group consisting of: none/A (1), none/I (2), none/Q (3), none/L (4), Y/S (14), K/R (18), H/R (24), and L/V (124); and
   b) the heavy-chain variable region has
      b1) the amino-acid sequence of SEQ ID NO: 2, or
      b2) the amino acid sequence of SEQ ID NO: 2 and further comprising at least one mutation selected from the group consisting of: none/Q (1), none/V (2), none/Q (3), none/L (4), none/Q (5), none/E (6), L/V (12), A/T (24), A/T (122), and V/L (123); and
   wherein the IgG is an IgG1 or an IgG2.

2. The IgG according to claim 1, wherein:
   the light-chain variable region has the amino-acid sequence of SEQ ID NO: 1, and
   the heavy-chain variable region has the amino-acid sequence of SEQ ID NO: 2.

3. The IgG according to claim 1, wherein the light-chain variable region has the amino-acid sequence of SEQ ID NO: 1, and further comprising at least one mutation selected from the group consisting of:
   none/A (1)
   none/I (2)
   none/Q (3)
   none/L (4)
   Y/S (14)
   K/R (18)
   H/R (24), and
   L/V (124).

4. The IgG according to claim 3, wherein the light-chain variable region of SEQ ID NO: 1 comprises the following mutations:
   none/A (1)
   none/I (2)
   none/Q (3)
   none/L (4)
   Y/S (14)
   K/R (18)
   H/R (24), and
   L/V (124).

5. The IgG according to claim 1, wherein the heavy-chain variable region has the amino-acid sequence of SEQ ID NO: 2, and further comprising at least one mutation selected from the group consisting of:
   none/Q (1)
   none/V (2)
   none/Q (3)
   none/L (4)
   none/Q (5)
   none/E (6)
   L/V (12)
   A/T (24)
   A/T (122), and
   V/L (123).

6. The IgG according to claim 5, wherein the heavy-chain variable region of SEQ ID NO: 2 comprises the following mutations:
   none/Q (1)
   none/V (2)
   none/Q (3)
   none/L (4)
   none/Q (5)
   none/E (6)
   L/V (12)
   A/T (24)
   A/T (122), and
   V/L (123).

7. The IgG according to claim 1, wherein the light chain constant region comprises the amino-acid sequence of SEQ ID NO: 3, and the heavy-chain constant region comprises the amino-acid sequence of SEQ ID NO: 4.

8. The IgG according to claim 1, wherein the constant region of each of the heavy chains thereof is of a γ1 type.

9. The IgG according to claim 1, wherein
   the constant region of each of the heavy chains thereof is of a γ1 type and comprises the amino-acid sequence encoded by the nucleic acid sequence SEQ ID NO: 9, and
   the constant region of each of the light chains thereof comprises the amino-acid sequence encoded by the nucleic acid sequence SEQ ID NO: 10.

10. The IgG according to claim 1, wherein
    each of the light chains thereof comprises the amino-acid sequence encoded by the nucleic acid sequence SEQ ID NO: 11, and
    each of the heavy chains thereof comprises the amino-acid sequence encoded by the nucleic acid sequence SEQ ID NO: 12.

11. A composition comprising at least one human IgG according to claim 1.

12. A pharmaceutical composition comprising at least one human IgG according to claim 1 and a pharmaceutically acceptable vehicle.

13. A medicament comprising a human IgG according to claim 1 for treating an infection with *Bacillus anthracis*.

14. A kit for detecting a protective antigen-containing anthrax toxin, comprising:
    a first container containing at least one labeled IgG according to claim 1, and
    a second container containing a means for detecting said labeled IgG.

15. An immunoconjugate, comprising the IgG according to claim 1 bound to a therapeutic agent.

* * * * *